US005576428A

United States Patent [19]
Butler et al.

[11] Patent Number: 5,576,428
[45] Date of Patent: Nov. 19, 1996

[54] INVERTASE GENE(S) AND USES THEREOF

[75] Inventors: William O. Butler, San Diego, Calif.; Yoshihiro Konno, Gunma, Japan; Craig D. Dickinson, San Diego, Calif.; Leona C. Fitzmaurice, San Diego, Calif.; Theodore E. Mirkov, San Diego, Calif.; Kathryn J. Elliott, San Diego, Calif.

[73] Assignee: The Salk Institute Biotechnology/Industrial Associates, Inc., La Jolla, Calif.

[21] Appl. No.: 107,748

[22] Filed: Aug. 20, 1993

Related U.S. Application Data

[63] Continuation of PCT/US92/01385, Feb. 21, 1992, which is a continuation-in-part of Ser. No. 771,331, Oct. 4, 1991, abandoned, which is a continuation-in-part of Ser. No. 660,344, Feb. 22, 1991, abandoned.

[51] Int. Cl.$^6$ ............................. C07H 21/04; C12N 15/11; C12N 15/29; C12N 15/82
[52] U.S. Cl. ..................... 536/24.1; 536/23.6; 435/69.1; 435/172.3; 935/35
[58] Field of Search ............................. 536/24.1, 23.6; 935/35; 435/69.1, 172.3

[56] References Cited

U.S. PATENT DOCUMENTS

| | | | |
|---|---|---|---|
| 4,394,443 | 7/1984 | Weissman et al. | 435/6 |
| 4,446,235 | 5/1984 | Seeburg | 435/91 |
| 4,801,540 | 1/1989 | Hiatt et al. | 435/172.3 |
| 4,943,674 | 6/1990 | Houck et al. | 800/205 |
| 5,107,065 | 4/1992 | Shewmaker et al. | 800/205 |
| 5,254,800 | 10/1993 | Bird et al. | 800/205 |

FOREIGN PATENT DOCUMENTS

| | | |
|---|---|---|
| 0332104 | 9/1989 | European Pat. Off. |
| 0442592 | 8/1991 | European Pat. Off. |
| 8912059 | 12/1989 | WIPO |
| 8912230 | 12/1989 | WIPO |
| 8912386 | 12/1989 | WIPO |
| 9105865 | 5/1991 | WIPO |
| 9307257 | 4/1993 | WIPO |
| 9306711 | 4/1993 | WIPO |

OTHER PUBLICATIONS

Davies et al. "Identification of cDNA clones for tomato (*Lycopersicon esculentum* Mill.) mRNAs that accumulate during furit ripening and leaf senescence in response to ethylene", *Planta* 179:73–80 (1989).

Gray et al., "Molecular biology of fruit ripening and its manipulation with antisense genes", *Plant Molecular Biology* 19:69–87 (1992).

Plant Molecular Biology, vol. 21, 1993, pp. 515–524, "Isolation And Characterization Of Fruit Vacuolar Invertase Genes From Two Tomato Species And Temporal Differences In mRNA Levels During Fruit Ripening", Kathryn J. Elliott et al.

Iwatsubo, et al., "The development of activity of cell wall bound β–fructofuranosidase with ripening and senescence to tomato fruit," *Agr. Biol. Chem.*, 39(4): 907–908 (1975).

Iwatsubo, et al., "Increase of β–fructofuranosidase content in tomato fruit during the ripening process," *Agr. Biol. Chem.*, 40(6): 1243–1244 (1976).

Nakagawa, et al., "Purification and some properties of two types of β–fructofuranosidase from tomato fruit," *Agr. Biol. Chem.*, 36: 18–26 (1971).

Sturm, et al., "cDNA cloning of carrot extracellular β–fructosidase and its expression in response to wounding and bacterial infection," *Plant Cell*, 2: 1107–1119 (1990).

Dickinsen, et al., "Slow–growth phenotype of transgenic tomato expressing apoplastic invertase," *Plant Physiology*, 95: 420–425 (1991).

Endo, et al., "Size and levels of mRNA for acid invertase in ripe tomato fruit," *Plant Cell Physiology*, 31(5): 655–659 (1990).

Manning, et al., "Distribution of acid invertase in the tomato plant," *Phytochemistry*, 14: 1965–1969 (1975).

Takehana, et al., "Purification of some properties of β–fructofuranosidase from from tomato fruit," *Bull Fac Hort, Chiba Univ.*, 18: 67–76 (1970).

Yelle, et al., "Genetic and biochemical analysis of sucrose accumulation in tomato fruit (Abstract No. 49)," *Horticultural Biotechnology Symposium, Univ. of Calif.*, Aug. 21–23 (1989).

Bracho, et al., "Purification and partial characterization of potato (*Soanum tuberosum*) invertase and its endogenous proteinaceous inhibitor," *Plant Physiology*, 92: 386–394 (1990).

Faye, et al., "Evidence for the glycoprotein nature of radish β–fructosidase," *Biochimie*, 61:51–59 (1979).

(List continued on next page.)

*Primary Examiner*—Patricia R. Moody
*Attorney, Agent, or Firm*—Burns, Doane, Swecker & Mathis, LLP

[57] ABSTRACT

Transgenic plants that are modified to produce fruits that have altered levels of soluble solids compared to non-transgenic plants of the same species are provided. The transgenic plants are prepared by introducing into plants DNA constructs that encode invertase operatively linked to DNA encoding regulatory regions that direct transcription of the DNA encoding invertase and operatively linked to DNA encoding amino acids that direct proper processing of the invertase through the secretory pathways of the plant and targeting of the invertase to the vacuole.

In particular, DNA constructs encoding tomato plant vacuolar invertase in operative linkage with a developmentally regulated promoter region are provided. Preferred regulatory and structural DNA is obtained from genomic DNA clones and cDNA clones encoding tomato fruit vacuolar invertases from the commercial tomato plant, *Lycopersicon esculentum*, and wild tomato plant, *Lycopersicon pimpinellifolium*.

Probes derived from the genomic DNA and cDNA, antibodies specific for tomato fruit invertase, and uses therefor, are also provided.

13 Claims, No Drawings

OTHER PUBLICATIONS

Karuppiah, et al., "Purification and characterization of souble (cytosolic) and bound (cell wall) isoforms of invertase in barley (*Hordium volgare*) enlongating stem tissue," *Plant Physiology*, 91:993–998 (1989).

Lauriere, et al., "Characterization of β–fructosidase, an extra–cellular glycoprotein of carrot cells," *Biochimie*, 70: 1483–1491 (1988).

Leigh, et al., "The localization of acid invertase activity and sucrose in the vacuoles of storage roots of bettroot (*Beta vulgaris*)," *Biochem. J.*, 178: 593–547 (1979).

Prado, et al., "Purification and characterization of *Ricinus communis* invertase," *Journal of Biological Chemistry*, 260(8): 4952–4957 (1985).

von Schaewen, et al., "Expression of a yeast–derived invertase in the cell wall of tobacco and Arabiodopsis plants leads to accumulation of carbohydrate and inhibition of photosynthesis and strongly influences growth and phenotype of transgenic tobacco plants," *The EMBO Journal*, 9(10): 3033–3044 (1990).

Morton, et al., "Monoclonal Antibody identifies a 200–kDa subunit of the dihydropyridine–sensitive calcium channel," *Journal of Biological Chemistry*, 262(25): 11904–11907 (1987).

Lichtenstein, "Anti–sense RNA as a tool to study plant gene expression," *Nature*, 333: 801–802 (1988).

Bednarek, et al., "A carboxyl–terminal propeptide is necessary for proper sorting of barley lectin to vacuoles of tobacco," *Plant Cell*, 2: 1145–1155 (1990).

Crum, et al., "Complementary oligodeoxynucleotide mediated inhibition of tobacco mosaic virus RNA translation in vitro," *Nucl. Acids Res.*, 16(10: 4569–4581 (1988).

Freeman, et al., "A comparison of methods for plasmid delivery into plant protoplasts," *Plant & Cell Physiol.*, 25(8): 1353–1365 (1984).

Lorz, et al., "Gene transfer to cereal cells mediated by protoplast transformation," *Mol. Gen. Genet.*, 199: 178–182 (1985).

Krens, et al., "In vitro transformation of plant protoplast with Ti–plasmid DNA," *Nature*, 296: 72–74 (1982).

Tague, et al., "A short domain of the plant vacuolar protein phytohemagglutinin targets invertase to the yeast vacuole," *Plant Cell*, 2: 553–546 (1990).

Yelle, et al., "Sink metabolism in tomato fruit," *Plant Physiol.*, 95: 1026–1035 (1991).

Faye, et al., "Structure, biosynthesis, and function of asparagine–linked glycans on plant glycoproteins," *Physiologia Plantarum*, 75: 309–314 (1989).

Willmitzer, et al., "Transgenic plants with altered habit and/or yield–containing DNA coding for products capable of altering photoassimilate distribution and/or production," *Derwent World Patents Index WPI* Accession No. 91–246636.

Chrispeels, "Sorting of protein in the secretory system," *Ann. Rev. Plant. Physiol. Plant Molec. Biol.*, 42: 21–53 (1991).

Saalbach, et al., "Different legumin protein domains act as vacuolar targeting signals," *Plant Cell*, 3: 695–708 (1991).

Bustos, et al., "Regulation of β–glucuronidase expression in transgenic tobacco plants by A/T–rich cis–acting sequence found upstream of a French bean β–phaseolin gene," *Plant Cell*, 1: 839–853 (1989).

Callis, et al., "Introns increase gene expression in cultured maize cells," *Genes Dev.* 1: 1183–1200 (1987).

DeLoose, et al., "Primary stgructure of a hormonally regulated β–glucanase of *Nicotiana plumbaginifolia*," *Gene*, 70: 13–23 (1988).

Forde, et al. "Nuclear factors interact with conserved A/T–rich elements upstream of a nodule–enhanced glutamine synthetase gene from French bean," *Plant Cell*, 2: 925–939 (1990).

Giaquinta, et al., "Pathway of phloem unloading of sucrose in corn roots," *Plant Physiol.*, 72: 362–367 (1983).

Jensen, et al., "Interaction of a nodule specific, trans–acting factor with distinct DNA elements in the soybean leghaemoglobin lbc$_3$ 5' upstream region," *EMBO J.*, 7: 1265–1271 (1988).

Jofuku, et al., "Interaction of an embryo DNA binding protein with a soybean lectin gene upstream region," *Nature*, 328: 734–737 (1987).

Joshi, C. P., "An inspection of the domain between putative TATA box and translation start site in 79 plant genes," *Nucl. Acids. Res.*, 15: 6643–6653 (1987a).

Joshi, C. P., "Putative polyadenylation signals in nuclear genes of higher plants: a compilation and analysis." *Nucl. Acids Res.*, 15: 9627–9640 (1987b).

Martin, et al., "Characterization of the levanase gene of *Bacillus subtillis* which shows homology to yeast invertase," *Mol. Gen. Gent.*, 208: 177–184 (1987).

McElroy, et al., "Isolation of an efficient actin promoter for use in rice transformation," *Plant Cell*, 2: 163–171 (1990.

Miron, et al., "Sucrose phosphate synthase, sucrose synthase, and invertase activities in developing fruit of *Lycopersicon esculentum* Mill. and the sucrose accumulating *Lycopersicon hirsutum* Humb. and Bonpl.," *Plant Physiol.*, 95: 623–627 (1991).

Ricardo, C. P. P., "Alkaline β–fructofuranosidases of tuberous roots: Possible physiological function," *Planta*, 118: 333–343 (1974).

Ricardo, et al., "Development of tuberous roots and sugar accumulation as related to invertase activity and mineral nutrition," *Planta*, 118: 43–55 (1974).

von Heijne, G., "A new method for predicting signal sequence cleavage sites," *Nucl. Acids Res.*, 14: 4683–4690 (1986).

Boller, et al., "Hydrolytic enzymes in the central vacuole of plant cells," *Plant Physiol.*, 63: 1123–1132 (1979).

Esmon, et al., "Structure, assembly, and secretion of octameric invertase," *J. Biol. Chem.*, 262: 4387–4394 (1987).

Dean et al., "mRNA transcripts of several plant genes thatare polyadenylated at muliple sites in vivo," *Ucle. Acids Res.* 14:2229–2240 (1986).

Klann et al., "Tomato Fruit Acid Invertase Complementary cDNA", Plant Physiology 99:351–353 (1992).

Jorgensen, "Altered gene expression in plants to trans interactions betweenhomologous genes", *Trends in Biotech.* 8:340–344.

Tieman et al., "An Antisense Pectin Methylesterase gene Alters Pectin Chemistry and Soluble Solids in Tomato Fruit", *The Plant Cell* 4:657–679.

Atanassov et al. (1983), in Handbook of Plant Cell Culture, vol. 4, Evans et al. (ed), MacMillan Pub. Co., pp. 652–665.

Shahin (1984), in Cell Culture and Somatic Cell genetics of Plants, vol. 1 Vasil (ed), pp. 370–371.

Goldenberg et al. (1966) *Genetics* 2, pp. 1 and 9 and Table 7.

Vaaler et al., "Pyridoxal 5'–Phsophate–dependent Histidine Decarboxylase", *J. Biol. Chem.* 261:11010–11013.

Rick, "High Soluble–Solids content in Large–Fruited Tomato Lines Derived from a Wild Green–Fruited Species", *Hilgardia* 42:493–510.

Stoforos et al. (1992) *J. Food Science* 57:707–713.:.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2199 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..1917
        ( D ) OTHER INFORMATION: /product="L. esculentum vacuolar invertase"

( x i ) SEQUENCE DESCRIPTION: SEQ ID NO:1:

```
TCTATT ATG GCC ACT CAG TGT TAT GAC CCC GAA AAC TCC GCC TCT CGT        48
       Met Ala Thr Gln Cys Tyr Asp Pro Glu Asn Ser Ala Ser Arg
        1               5                  10

TAC ACA TTA CTC CCG GAT CAA CCC GAT TCC GGC CAC CGG AAG TCC CTT        96
Tyr Thr Leu Leu Pro Asp Gln Pro Asp Ser Gly His Arg Lys Ser Leu
 15              20                  25                  30

AAA ATC ATC TCC GGC ATT TTC CTC TCC GTT TTC CTT TTG CTT TCT GTA       144
Lys Ile Ile Ser Gly Ile Phe Leu Ser Val Phe Leu Leu Leu Ser Val
                 35                  40                  45

GCC TTC TTT CCG ATC CTC AAC AAC CAG TCA CCG GAC TTG CAA ATC GAC       192
Ala Phe Phe Pro Ile Leu Asn Asn Gln Ser Pro Asp Leu Gln Ile Asp
             50                  55                  60

TCC CGT TCG CCG GCG CCG CCG TCA AGA GGT GTT TCT CAG GGA GTC TCC       240
Ser Arg Ser Pro Ala Pro Pro Ser Arg Gly Val Ser Gln Gly Val Ser
         65                  70                  75

GAT AAA ACT TTT CGA GAT GTA GCC GGT GCT AGT CAC GTT TCT TAT GCG       288
Asp Lys Thr Phe Arg Asp Val Ala Gly Ala Ser His Val Ser Tyr Ala
     80                  85                  90

TGG TCC AAT GCT ATG CTT AGC TGG CAA AGA ACG GCT TAC CAT TTT CAA       336
Trp Ser Asn Ala Met Leu Ser Trp Gln Arg Thr Ala Tyr His Phe Gln
 95                 100                 105                 110

CCT CAA AAA AAT TGG ATG AAC GAT CCT AAT GGA CCA TTG TAT CAC AAG       384
Pro Gln Lys Asn Trp Met Asn Asp Pro Asn Gly Pro Leu Tyr His Lys
                115                 120                 125

GGA TGG TAC CAC CTT TTT TAT CAA TAC AAT CCA GAT TCA GCT ATT TGG       432
Gly Trp Tyr His Leu Phe Tyr Gln Tyr Asn Pro Asp Ser Ala Ile Trp
            130                 135                 140

GGA AAT ATC ACA TGG GGC CAT GCT GTA TCC AAG GAC TTG ATC CAC TGG       480
Gly Asn Ile Thr Trp Gly His Ala Val Ser Lys Asp Leu Ile His Trp
        145                 150                 155
```

| | | | | | | | | | | | | | | | | |
|---|---|---|---|---|---|---|---|---|---|---|---|---|---|---|---|---|
| CTC | TAC | TTG | CCT | TTT | GCC | ATG | GTT | CCT | GAT | CAA | TGG | TAT | GAT | ATT | AAC | 528 |
| Leu | Tyr | Leu | Pro | Phe | Ala | Met | Val | Pro | Asp | Gln | Trp | Tyr | Asp | Ile | Asn | |
| 160 | | | | | 165 | | | | | 170 | | | | | | |
| GGT | GTC | TGG | ACA | GGG | TCC | GCT | ACC | ATC | CTA | CCC | GAT | GGT | CAG | ATC | ATG | 576 |
| Gly | Val | Trp | Thr | Gly | Ser | Ala | Thr | Ile | Leu | Pro | Asp | Gly | Gln | Ile | Met | |
| 175 | | | | | 180 | | | | | 185 | | | | | 190 | |
| ATG | CTT | TAT | ACC | GGT | GAC | ACT | GAT | GAT | TAT | GTG | CAA | GTG | CAA | AAT | CTT | 624 |
| Met | Leu | Tyr | Thr | Gly | Asp | Thr | Asp | Asp | Tyr | Val | Gln | Val | Gln | Asn | Leu | |
| | | | | 195 | | | | | 200 | | | | | 205 | | |
| GCG | TAC | CCC | GCC | AAC | TTA | TCT | GAT | CCT | CTC | CTT | CTA | GAC | TGG | GTC | AAG | 672 |
| Ala | Tyr | Pro | Ala | Asn | Leu | Ser | Asp | Pro | Leu | Leu | Leu | Asp | Trp | Val | Lys | |
| | | | 210 | | | | | 215 | | | | | 220 | | | |
| TTC | AAA | GGC | AAC | CCG | GTT | CTG | GTT | CCT | CCA | CCC | GGC | ATT | GGT | GTC | AAG | 720 |
| Phe | Lys | Gly | Asn | Pro | Val | Leu | Val | Pro | Pro | Pro | Gly | Ile | Gly | Val | Lys | |
| | | 225 | | | | | 230 | | | | | 235 | | | | |
| GAC | TTT | AGA | GAC | CCG | ACT | ACT | GCT | TGG | ACC | GGA | CCA | CAA | AAT | GGG | CAA | 768 |
| Asp | Phe | Arg | Asp | Pro | Thr | Thr | Ala | Trp | Thr | Gly | Pro | Gln | Asn | Gly | Gln | |
| | 240 | | | | | 245 | | | | | 250 | | | | | |
| TGG | CTG | TTA | ACA | ATC | GGG | TCT | AAG | ATT | GGT | AAA | ACG | GGT | GTT | GCA | CTT | 816 |
| Trp | Leu | Leu | Thr | Ile | Gly | Ser | Lys | Ile | Gly | Lys | Thr | Gly | Val | Ala | Leu | |
| 255 | | | | | 260 | | | | | 265 | | | | | 270 | |
| GTT | TAT | GAA | ACT | TCC | AAC | TTC | ACA | AGC | TTT | AAG | CTA | TTG | GAT | GGA | GTG | 864 |
| Val | Tyr | Glu | Thr | Ser | Asn | Phe | Thr | Ser | Phe | Lys | Leu | Leu | Asp | Gly | Val | |
| | | | | 275 | | | | | 280 | | | | | 285 | | |
| CTG | CAT | GCG | GTT | CCG | GGT | ACG | GGT | ATG | TGG | GAG | TGT | GTG | GAC | TTT | TAC | 912 |
| Leu | His | Ala | Val | Pro | Gly | Thr | Gly | Met | Trp | Glu | Cys | Val | Asp | Phe | Tyr | |
| | | | | 290 | | | | | 295 | | | | | 300 | | |
| CCG | GTA | TCT | ACT | AAA | AAA | ACA | AAC | GGG | TTG | GAC | ACA | TCA | TAT | AAC | GGG | 960 |
| Pro | Val | Ser | Thr | Lys | Lys | Thr | Asn | Gly | Leu | Asp | Thr | Ser | Tyr | Asn | Gly | |
| | | | 305 | | | | | 310 | | | | | 315 | | | |
| CCG | GGT | GTA | AAG | CAT | GTG | TTA | AAA | GCA | AGT | TTA | GAT | GAC | AAT | AAG | CAA | 1008 |
| Pro | Gly | Val | Lys | His | Val | Leu | Lys | Ala | Ser | Leu | Asp | Asp | Asn | Lys | Gln | |
| | | | 320 | | | | | 325 | | | | | 330 | | | |
| GAT | CAT | TAT | GCT | ATT | GGT | ACG | TAT | GAC | TTG | GGA | AAG | AAC | AAA | TGG | ACA | 1056 |
| Asp | His | Tyr | Ala | Ile | Gly | Thr | Tyr | Asp | Leu | Gly | Lys | Asn | Lys | Trp | Thr | |
| 335 | | | | | 340 | | | | | 345 | | | | | 350 | |
| CCC | GAT | AAC | CCG | GAA | TTG | GAT | TGT | GGA | ATT | GGG | TTG | AGA | CTA | GAC | TAT | 1104 |
| Pro | Asp | Asn | Pro | Glu | Leu | Asp | Cys | Gly | Ile | Gly | Leu | Arg | Leu | Asp | Tyr | |
| | | | | 355 | | | | | 360 | | | | | 365 | | |
| GGG | AAA | TAT | TAT | GCA | TCA | AAG | ACT | TTT | TAT | GAC | CCG | AAG | AAA | GAA | CGA | 1152 |
| Gly | Lys | Tyr | Tyr | Ala | Ser | Lys | Thr | Phe | Tyr | Asp | Pro | Lys | Lys | Glu | Arg | |
| | | | 370 | | | | | 375 | | | | | 380 | | | |
| AGA | GTA | CTG | TGG | GGA | TGG | ATT | GGG | GAA | ACT | GAC | AGT | GAA | TCT | GCT | GAC | 1200 |
| Arg | Val | Leu | Trp | Gly | Trp | Ile | Gly | Glu | Thr | Asp | Ser | Glu | Ser | Ala | Asp | |
| | | 385 | | | | | 390 | | | | | 395 | | | | |
| CTG | CAG | AAG | GGA | TGG | GCA | TCT | GTA | CAG | AGT | ATT | CCA | AGG | ACA | GTG | CTT | 1248 |
| Leu | Gln | Lys | Gly | Trp | Ala | Ser | Val | Gln | Ser | Ile | Pro | Arg | Thr | Val | Leu | |
| | 400 | | | | | 405 | | | | | 410 | | | | | |
| TAC | GAC | AAG | AAG | ACA | GGG | ACA | CAT | CTA | CTT | CAG | TGG | CCA | GTG | GAA | GAA | 1296 |
| Tyr | Asp | Lys | Lys | Thr | Gly | Thr | His | Leu | Leu | Gln | Trp | Pro | Val | Glu | Glu | |
| 415 | | | | | 420 | | | | | 425 | | | | | 430 | |
| ATT | GAA | AGC | TTA | AGA | GTG | GGT | GAT | CCT | ACT | GTT | AAG | CAA | GTC | GAT | CTT | 1344 |
| Ile | Glu | Ser | Leu | Arg | Val | Gly | Asp | Pro | Thr | Val | Lys | Gln | Val | Asp | Leu | |
| | | | | 435 | | | | | 440 | | | | | 445 | | |
| CAA | CCA | GGC | TCA | ATT | GAG | CTA | CTC | CGT | GTT | GAC | TCA | GCT | GCA | GAG | TTG | 1392 |
| Gln | Pro | Gly | Ser | Ile | Glu | Leu | Leu | Arg | Val | Asp | Ser | Ala | Ala | Glu | Leu | |
| | | | 450 | | | | | 455 | | | | | 460 | | | |
| GAT | ATA | GAA | GCC | TCA | TTT | GAA | GTG | GAC | AAA | GTC | GCG | CTT | CAG | GGA | ATA | 1440 |
| Asp | Ile | Glu | Ala | Ser | Phe | Glu | Val | Asp | Lys | Val | Ala | Leu | Gln | Gly | Ile | |
| | | 465 | | | | | 470 | | | | | 475 | | | | |

| | | | | | | | | | | | | | | | | |
|---|---|---|---|---|---|---|---|---|---|---|---|---|---|---|---|---|
| ATT | GAA | GCA | GAT | CAT | GTA | GGT | TTC | AGT | TGC | TCT | ACT | AGT | GGA | GGT | GCT | 1488 |
| Ile | Glu | Ala | Asp | His | Val | Gly | Phe | Ser | Cys | Ser | Thr | Ser | Gly | Gly | Ala | |
| 480 | | | | | 485 | | | | | 490 | | | | | | |
| GCT | AGC | AGA | GGC | ATT | TTG | GGA | CCA | TTT | GGT | GTC | ATA | GTA | ATT | GCT | GAT | 1536 |
| Ala | Ser | Arg | Gly | Ile | Leu | Gly | Pro | Phe | Gly | Val | Ile | Val | Ile | Ala | Asp | |
| 495 | | | | | 500 | | | | | 505 | | | | | 510 | |
| CAA | ACG | CTA | TCT | GAG | CTA | ACG | CCA | GTT | TAC | TTT | TAC | ATT | TCT | AAA | GGA | 1584 |
| Gln | Thr | Leu | Ser | Glu | Leu | Thr | Pro | Val | Tyr | Phe | Tyr | Ile | Ser | Lys | Gly | |
| | | | | 515 | | | | | 520 | | | | | 525 | | |
| GCT | GAT | GGT | CGT | GCA | GAG | ACT | CAC | TTC | TGT | GCT | GAT | CAA | ACT | AGA | TCC | 1632 |
| Ala | Asp | Gly | Arg | Ala | Glu | Thr | His | Phe | Cys | Ala | Asp | Gln | Thr | Arg | Ser | |
| | | | 530 | | | | | 535 | | | | | 540 | | | |
| TCT | GAG | GCT | CCG | GGA | GTT | GGT | AAA | CAA | GTT | TAT | GGT | AGT | TCA | GTA | CCT | 1680 |
| Ser | Glu | Ala | Pro | Gly | Val | Gly | Lys | Gln | Val | Tyr | Gly | Ser | Ser | Val | Pro | |
| | | 545 | | | | | 550 | | | | | 555 | | | | |
| GTG | TTG | GAC | GGT | GAA | AAA | CAT | TCA | ATG | AGA | TTA | TTG | GTG | GAT | CAC | TCA | 1728 |
| Val | Leu | Asp | Gly | Glu | Lys | His | Ser | Met | Arg | Leu | Leu | Val | Asp | His | Ser | |
| | 560 | | | | | 565 | | | | | 570 | | | | | |
| ATT | GTG | GAG | AGC | TTT | GCT | CAA | GGA | GGA | AGA | ACA | GTC | ATA | ACA | TCG | CGA | 1776 |
| Ile | Val | Glu | Ser | Phe | Ala | Gln | Gly | Gly | Arg | Thr | Val | Ile | Thr | Ser | Arg | |
| 575 | | | | | 580 | | | | | 585 | | | | | 590 | |
| ATT | TAC | CCA | ACA | AAG | GCA | GTA | AAT | GGA | GCA | GCA | CGA | CTC | TTT | GTT | TTC | 1824 |
| Ile | Tyr | Pro | Thr | Lys | Ala | Val | Asn | Gly | Ala | Ala | Arg | Leu | Phe | Val | Phe | |
| | | | | 595 | | | | | 600 | | | | | 605 | | |
| AAC | AAT | GCC | ACA | GGG | GCT | AGC | GTT | ACT | GCC | TCC | GTC | AAG | ATT | TGG | TCA | 1872 |
| Asn | Asn | Ala | Thr | Gly | Ala | Ser | Val | Thr | Ala | Ser | Val | Lys | Ile | Trp | Ser | |
| | | | 610 | | | | | 615 | | | | | 620 | | | |
| CTT | GAG | TCA | GCT | AAT | ATT | CAA | TCC | TTC | CCT | TTG | CAA | GAC | TTG | TAATCTTCTT | | 1924 |
| Leu | Glu | Ser | Ala | Asn | Ile | Gln | Ser | Phe | Pro | Leu | Gln | Asp | Leu | | | |
| | | 625 | | | | | 630 | | | | | 635 | | | | |

```
TATTTCGTTT TTTTTTTCTT TTTCATTTGA AGGTTATTTC ACCGACGTCC CATCAAGAAA      1984

GGGAAGAGGG AGATCAATAT ATGTAGTGTT ATTCGCCCTA CCTTAGGATT AGATGTCATC      2044

TAGCAATGTC AAATCTAGTA GAGTATACAA TGTATGGGTT CCTGGAAACC GAGTAGAGCT     2104

TACCTGGATT CTATGTAAAC TAAGAAAGCT CAGCAAATAT ATGCACAAAT AATTTACAGA      2164

AACAACTTGG GAATGTTGAC AAAAAAAAAA AAAAA                                 2199
```

( 2 ) INFORMATION FOR SEQ ID NO:2:

( i ) SEQUENCE CHARACTERISTICS:
        ( A ) LENGTH: 10798 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Lycopersicon esculentum ( i x ) FEATURE:
        ( A ) NAME/KEY: precursor_RNA
        ( B ) LOCATION: 3520..7445

( x i ) SEQUENCE DESCRIPTION: SEQ ID NO:2:

```
GATCTCGATA AGTTATGTCT TGTTGGAATC GATATCAAAT AACCGTCGAC GGTATCTTTG       60

ATATGAGGTA GCGCTCAATG ATATAAATTG TGATGAGGAT CTTGAATTCA AATCTGTCAT      120

ATAGTGTGAA CAGATAAATG GTTAGCCAAG TAAAATGCAC AATTCAAGTA TATTTTGTTT      180

CACTTAGAAA AGTGACATTT TGGACTGGTA GTCCATAAAT CAAGGTATAA TGTCAGTGGG      240

GTACAAATAA ATTATTATGT GATAGTATAA CCGTAAGATA TCAAATACGG TTTGTGCCTT      300
```

```
GGGGCATAAA  GGTTTATCGC  AAAAATCCTG  ACATTATTGG  AGATGTTTTC  TCCTTTGGTG   360
GATGCAATGA  GGTTTGTTTT  GATCTGGCAA  CATATGAAAA  ACTTGAATGC  ATGTAATGAA   420
AAATTGTAAT  GAAGGTTATA  TGAAAATCCT  TGAAACAATC  CAGGTGTCTG  AAGCATATAA   480
AGGTTGAAAG  AAACTTATCC  AATAAAGCTT  CAAGAATCCT  TATATGGATT  GAAATAGTCA   540
AGGAAGAAAA  AGGGTACAAA  AGAATGACCC  TAATTGTCCT  TGTATTTTTA  TGAAAAGGTC   600
TTGGTAAGAC  AAAATTTTGT  CTTGACCTAC  AGATTGTTAA  TTTGACAAAT  AAAATATTTG   660
TCTAACAGAC  AACAGTGCAC  ATACACTGAA  AAATTTTGAT  GCAATTTTAT  GTGGATATAT   720
CGCATTCATT  GAGTACCCCA  ATGATTATGA  GATCACTTGA  CATAAATGAT  GATTCAGTTT   780
GATCTCAAAA  GAAGGATAAG  AGTTTCTTGG  TGATGAAACT  CTATCTTGGT  GCAATGAGGG   840
CACTAGTGCA  TCTTACTAAC  AATATTTGAC  TAGATATTTG  TTTTGCAGTA  AATTTACTGG   900
CAAGATTCAG  TTTCTCCCCG  ATAAAGGAC  ATTGAAATGG  TGTTGAGCAC  ATGAATGAAT    960
ATCCTCAAAG  GACCATAGTT  ATGGGTTTAT  TCTATCCCGA  GGAATCCAAG  ACAAAATTGA   1020
TTGATTACGC  AGATGCAGAA  TATTTATCTG  ATCCGCATAA  AGCTCTATCT  CAAGCACGCT   1080
ATGTGTTTGC  ATGTGGAGGC  ACAATAATAT  CCTGGGGATC  AATGAAGCAA  ATGTTGCTCT   1140
GCAGAAATAA  AAGTCCTCCA  TGAAGCAAGT  CAAAAGTGCG  TCTGGTTGAG  ATAAATGACA   1200
CACCATATTC  AAGAAATGTG  TGGTTTTTCT  TTAAAAAAG  AATATACCAA  CCACAATGTA    1260
CAAAGATTGG  AGACATCATC  ACAAGAAATC  AAGTGATGTT  TTAATCAGGG  GGAGTACAAT   1320
ACGCGTTGCA  CTCTTTTTCC  CTTGATCGAG  GTTTTTTCC  CACTGGATTT  TCCTGACAAG    1380
GTTTTTAATG  AGGCAACAAA  TGGTGCGTAT  CAAAAGATAT  GTGTACTCTT  TTTCCTTCAC   1440
TAGAATTTTT  TCCCACAGGG  TTTTTCCTAG  TAAGGTTTTA  ACGAGGCACA  TTATCTATGG   1500
ACATCCAAGG  GGGAGTGTTA  TAAATACATT  GAATTAAGTG  GATAGTCCAT  AAGGTTGGCA   1560
 CATGAACAAC  CATTCATATT  CACTAGGTGA  CATGAACCTT  TTGGATAAG  AATGTATCTA   1620
TTTATTATGA  TACTTAATAT  GGTAATCTTT  GGAGTGATTT  CTCACTCTAT  AAATAGAGTT   1680
GTTCATTCAC  TATTGTAATA  TATACATATG  AGACTTGAAT  ACACTTGAAT  ACGAAGAAAG   1740
TCTTATCTTC  CATCTTACTT  CTCTTGTCTT  CTCTCTTTAT  GATTATATTC  TTATGAGCTT   1800
GATTTTATAA  CACGAATCTC  ATTATACGAA  AAGTTTTACT  ATTTATATTT  AATTAATAGA   1860
GGATTTAAAC  TTTTTAAATT  TCTGTCTTTA  TAGATGAGAA  CTTGTCTTTT  TGTTGAATCC   1920
AACTAAACAT  TCAATGAAGA  CAAATCAACC  TGTAAATCCC  TTTCAAGTAG  GATTTATTCG   1980
AATCTCATTA  TACGAAAAGT  TTTACTATTT  ATATTTAATT  AATAGAGGAT  TTAAACTTTT   2040
TAAATTTCTG  TCTTTATAGA  TGAGAACTTG  TCTTTTGTT  GAATCCAACT  AAACATTCAA    2100
TGAAGACAAA  TCAACCTGTA  AATCCCTTTC  AAGTAGGATT  TATTCGAATC  TCATTATACG   2160
AAAAGTTTTA  CTATTTATAT  TTAATTAATA  GAGAATTTAA  ACTTTTAAA  TTTCTGTCTT    2220
TATAGATGAG  AACTTGTCTT  TTTGTTGAAT  CCAACTAAAC  ATTCAATGAA  TACAAATCAA   2280
CCTGTAAATC  CCTTTCAAGT  AGGATTTATT  CGAATCTCAT  TATACGAAAA  GTTTTACTAT   2340
TTATATTTAA  TTAATAGAGA  ATTTAAACTT  TTTAAATTTC  TGTCTTTATA  GATGAGAACT   2400
TGTCTTTTTG  TTGAATCCAA  CTAAACATTC  AATGAATACA  AATCAACCTG  TAAATCCCTT   2460
TCAAGTAGGA  TTTATTCGAA  TCTCATTATA  CGAAAAGTTT  TACTATTTAT  ATTTAATTAA   2520
TAGAGAATTT  AAACTTTTTA  AATTTCTGTC  TTTATAGATG  AGAACTTGTC  TTTTGTTGA    2580
ATCCAACTAA  ACATTCAATG  AATACAAATC  AACCTGTAAA  TCCCTTTCAA  GTAGGATTTA   2640
TTCGAATCTC  ATTATACGAA  AAGTTTTACT  ATTTATATTT  AATTAATAGA  GAATTTAAAC   2700
```

| | | | | | | |
|---|---|---|---|---|---|---|
| TTTTTAAATT | TCTGTCTTTA | TAGATGAGAA | CTTGTCTTTT | TGTTGAATCC | AACTAAACAT | 2760 |
| TCAATGAATA | CAAATCAACC | TGTAAATCCC | TTTCAAGTAG | GATTTATTCG | AATCTCATTA | 2820 |
| TACGAAAAGT | TTTACTAGTT | ATATTTAATT | AATATTCAAG | TCTCAATTTT | TTTTAAATA | 2880 |
| TTTACATTCC | ACATTTTAAT | CTATAATGAA | AGTTACTAAA | ATATACTATC | AAGGAGAAAA | 2940 |
| TATACAAAAT | GGCCCATAAC | GATAGTCTTT | AATATATAAT | AAATATGTTC | ATTTGGATCC | 3000 |
| TTAATATATT | TCACTTGATT | AAAATAATAA | TAAATGTATA | ATAAAAGTG | GTCATTTTGG | 3060 |
| TCTTTTGTCC | TAAACATAGA | GTTTTTTTAC | CTTCAAAGAA | AAATCTTCCA | TAAAATCTAA | 3120 |
| TACTATTTTT | TTTTAATTTC | TCCAACAAAA | TTTATTATTT | TCTCTTTTAA | ATATTATTTT | 3180 |
| ACTGACCTAA | TAACAGTTTT | TATTTTGAGC | AAGAAAGTA | GTAAATTTTG | TTAAATAAAG | 3240 |
| AACCAAAATA | AATCATTTTA | ATCAAAGTAA | AATATAATAA | CGATTAAAAT | AAAGTATACA | 3300 |
| TTAAGTCATT | TCAATGAAGT | GAAATAAATG | AAGAAGTAAA | ATAAAAAAT | TAACCAAACA | 3360 |
| GTAAGCATAG | TTTTGGTCAT | TTTCTCTAAT | CCCAAGTGTA | CCTCAAATTA | TAAAAGTCCT | 3420 |
| TTTGTTACTC | AATTTCGTTG | GTCCCAGTCA | TTTTCTGTGT | TCATCACCTA | TATATATAGC | 3480 |
| AGTAGACTAG | TAGCTTCTCC | CATTCCTCTA | TCTTCTATTA | TGGCCACTCA | GTGTTATGAC | 3540 |
| CCCGAAAACT | CCGCCTCTCG | TTACACATTA | CTCCCGGATC | AACCCGATTC | CGGCCACCGG | 3600 |
| AAGTCCCTTA | AAATCATCTC | CGGCATTTTC | CTCTCCGTTT | TCCTTTTGCT | TTCTGTAGCC | 3660 |
| TTCTTTCCGA | TCCTCAACAA | CCAGTCACCG | GACTTGCAAA | TCGACTCCCG | TTCGCCGGCG | 3720 |
| CCGCCGTCAA | GAGGTGTTTC | TCAGGGAGTC | TCCGATAAAA | CTTTTCGAGA | TGTAGCCGGT | 3780 |
| GCTAGTCACG | TTTCTTATGC | GTGGTCCAAT | GCTATGCTTA | GCTGGCAAAG | AACGGCTTAC | 3840 |
| CATTTCAAC | CTCAAAAAAA | TTGGATGAAC | GGTAATTAAC | TTTCTTATTT | TGACTTTTCT | 3900 |
| TTAATTTCTT | TTTTATTTGA | TCTTAAAATT | GAAATTATTT | ATAAATACTT | ATAACAGTTC | 3960 |
| TTTTTTTTCT | CAATGATATT | TATGGCTATT | GATCTGTTGG | GGGTATCTTT | TGGATTCTGA | 4020 |
| TTGGATGCTA | TTCTGCAGAT | CCTAATGGTG | AGTTCAAAGT | TAATTATTAT | CACTATTTTC | 4080 |
| TGCTAGTTTT | TAATTAATTA | TATTCTTAAA | CTATGATTAT | AACTTTTAAA | GCAATCTCAT | 4140 |
| GAATGAGCAA | ATCATTAATT | CGGGTGCTTA | TGTATATCAT | CTCGGTTAAT | CCTTTTACCT | 4200 |
| TATACTCAAA | AACAAATATT | ACTCCCTTCA | AAATAATTGA | TGTTTGACAT | AATCAATGTG | 4260 |
| ATGTTTAATT | TTTTTTTCTT | TCAAATTTGC | CCTTCCTAAC | CCCTATAATG | ATTATGTCAA | 4320 |
| ATCCAAAGTG | AAAAGACTAT | CATAATTACA | TATGCTTTAG | TCACAATTAA | TTCATGTTAA | 4380 |
| ATCATCAATA | GTTTTGGATT | GGAGGGAGTA | CTCATTAGGA | AAAATAATTA | AGCTAAATCA | 4440 |
| TTCTTATTTT | CACTGTACAT | TATTTAGATT | AAGGGTGAAA | TAGGGGAGGA | ATCAATTATC | 4500 |
| TTATTTTTCT | AAATGGACAA | GTATTTGAA | ATAACAAATT | TTAAGAAAAC | ACGTCAAGTC | 4560 |
| AAATAGAGTA | GGATGGATGG | AGTAAATTCT | AACCTTTCTA | GATATTCATA | AAAATTAGTT | 4620 |
| GAACAGACAT | TTTAATAAAG | ACCACAAGTT | GATGAATTAA | GCTTGTTGTT | CCAATATAAT | 4680 |
| TGGATTAAC | ATGAGATCTT | GTGGCAGTAA | TGTTTTTTGC | TTTTGTGCAA | TTTTCCAATA | 4740 |
| AAAAGAAAAC | ACTTGATTGG | GTCAGTATTA | TACAAGTTTG | GAAACCAATC | ACGTTATGTG | 4800 |
| GGTCATACTT | TTTTGTAGTA | ATGTAATAAT | ACCAATAGTG | GGGCCCCAC | TCAAAGTAAT | 4860 |
| CCATCTTCCA | CTTGATTTTT | TTATTTTTTT | TTGAAATGGA | GTAGGTTATC | TTGGCCGCTT | 4920 |
| AGCAATTACT | ATTATCATGA | GTAAATGACG | GAAATTATAA | ATTTTTAAGA | TAAAATTATT | 4980 |
| ATTAATCTTT | TATAATTTTA | TGGTTATAAA | AGTCTCTCAA | ACTAATACAA | TAATATAAGC | 5040 |
| GCTGATACAT | GAGTCTGATG | TGCGAGATAC | ATTAATCTGA | TAGGTAAAAA | TGAGGAACTA | 5100 |

| | | | | | |
|---|---|---|---|---|---|
| GAAATTTATA | AAACTAATAT | GAATAATGAT | AATAAGATAA | CTTAAATGTG | AAATTTCTAT | 5160 |
| CATTTCTCCT | AACATACCAC | TAGTGAAATT | TGTTTACGTA | TCTTGTTGAA | GAAAATCTTA | 5220 |
| TCCAAAAGTC | AAAAATAAAA | ACTCGTGGCC | AAATTTTCAA | AAAAAAAGA | AGGTTATCTT | 5280 |
| TTTGCCGCAA | AAAGCATAGC | AATTTTGGTA | CGGAACGTAT | TGAGATTTTG | TAGAGTATTT | 5340 |
| TATAATTCAA | ATTGCATAGA | AAAGTCTTAC | CTATACAAGT | AAAAACTTTG | AAATTTCTAT | 5400 |
| TAACGTGAAT | AAATTGGTTA | ACAGGACCAT | TGTATCACAA | GGGATGGTAC | CACCTTTTT | 5460 |
| ATCAATACAA | TCCAGATTCA | GCTATTTGGG | GAAATATCAC | ATGGGGCCAT | GCTGTATCCA | 5520 |
| AGGACTTGAT | CCACTGGCTC | TACTTGCCTT | TTGCCATGGT | TCCTGATCAA | TGGTATGATA | 5580 |
| TTAACGGTGT | CTGGACAGGG | TCCGCTACCA | TCCTACCCGA | TGGTCAGATC | ATGATGCTTT | 5640 |
| ATACCGGTGA | CACTGATGAT | TATGTGCAAG | TGCAAAATCT | TGCGTACCCC | GCCAACTTAT | 5700 |
| CTGATCCTCT | CCTTCTAGAC | TGGGTCAAGT | TCAAAGGCAA | CCCGGTTCTG | GTTCCTCCAC | 5760 |
| CCGGCATTGG | TGTCAAGGAC | TTTAGAGACC | CGACTACTGC | TTGGACCGGA | CCACAAAATG | 5820 |
| GGCAATGGCT | GTTAACAATC | GGGTCTAAGA | TTGGTAAAAC | GGGTGTTGCA | CTTGTTTATG | 5880 |
| AAACTTCCAA | CTTCACAAGC | TTTAAGCTAT | GGATGGAGT | GCTGCATGCG | GTTCCGGGTA | 5940 |
| CGGGTATGTG | GGAGTGTGTG | GACTTTTACC | CGGTATCTAC | TAAAAAAACA | AACGGGTTGG | 6000 |
| ACACATCATA | TAACGGGCCG | GGTGTAAAGC | ATGTGTTAAA | AGCAAGTTTA | GATGACAATA | 6060 |
| AGCAAGATCA | TTATGCTATT | GGTACGTATG | ACTTGGGAAA | GAACAAATGG | ACACCCGATA | 6120 |
| ACCCGGAATT | GGATTGTGGA | ATTGGGTTGA | GACTAGACTA | TGGGAAATAT | TATGCATCAA | 6180 |
| AGACTTTTTA | TGACCCGAAG | AAAGAACGAA | GAGTACTGTG | GGATGGATT | GGGGAAACTG | 6240 |
| ACAGTGAATC | TGCTGACCTG | CAGAAGGGAT | GGGCATCTGT | ACAGGTATGG | ACTTGGATGA | 6300 |
| ACACATTGTT | TTGTTATTTT | ACTTTGCACC | ATACACAGCG | TCTAGTTGTA | TCGTAATAAT | 6360 |
| CATGGTAGGG | AAATTTCTTA | TTTAGAGAAA | GTTGTTATAA | TCAATGCATT | TGTAGGTGAA | 6420 |
| GTAAATTCTG | AATTGTATAT | GAAACGTGTC | TAATAGTGTT | TCGAAATAAC | AGAGTATTCC | 6480 |
| AAGGACAGTG | CTTTACGACA | AGAAGACAGG | GACACATCTA | CTTCAGTGGC | CAGTGGAAGA | 6540 |
| AATTGAAAGC | TTAAGAGTGG | GTGATCCTAC | TGTTAAGCAA | GTCGATCTTC | AACCAGGCTC | 6600 |
| AATTGAGCTA | CTCCGTGTTG | ACTCAGCTGC | AGAGGTTTGT | TGCGTTACTT | TTGTTTTAAA | 6660 |
| TTACAAACAC | GCGCTTAATC | TGCAGTCCCA | AAACTTGTTT | AGCTATTGTG | CAGTTGGATA | 6720 |
| TAGAAGCCTC | ATTTGAAGTG | GACAAAGTCG | CGCTTCAGGG | AATAATTGAA | GCAGATCATG | 6780 |
| TAGGTTTCAG | TTGCTCTACT | AGTGGAGGTG | CTGCTAGCAG | AGGCATTTTG | GGACCATTTG | 6840 |
| GTGTCATAGT | AATTGCTGAT | CAAACGCTAT | CTGAGCTAAC | GCCAGTTTAC | TTTTACATTT | 6900 |
| CTAAAGGAGC | TGATGGTCGT | GCAGAGACTC | ACTTCTGTGC | TGATCAAACT | AGGTTTGCTT | 6960 |
| TTCTATCTGG | CACAATTAAT | TTGTCCTTGT | AAAATGGAGA | TGGATAAAAG | TAGCGGGTTG | 7020 |
| TTGATCTGAT | ATATGCAGAT | CCTCTGAGGC | TCCGGGAGTT | GGTAAACAAG | TTTATGGTAG | 7080 |
| TTCAGTACCT | GTGTTGGACG | GTGAAAAACA | TTCAATGAGA | TTATTGGTAA | GTGATAATGA | 7140 |
| TTCCCTTATT | TTACCTTGAT | TTATTCCAT | TTCTTCACTT | CACAATAATT | AAAGTACTTG | 7200 |
| GCAGTTGCAT | TTGAGTAAAA | GGTTTTTAT | AAACTGAATT | TTAGGTGGAT | CACTCAATTG | 7260 |
| TGGAGAGCTT | TGCTCAAGGA | GGAAGAACAG | TCATAACATC | GCGAATTTAC | CCAACAAAGG | 7320 |
| CAGTAAATGG | AGCAGCACGA | CTCTTTGTTT | TCAACAATGC | CACAGGGGCT | AGCGTTACTG | 7380 |
| CCTCCGTCAA | GATTTGGTCA | CTTGAGTCAG | CTAATATTCA | ATCCTTCCCT | TTGCAAGACT | 7440 |
| TGTAATCTTC | TTTATTTCGT | TTTTTTTTC | TTTTTCATTT | GAAGGTTATT | TCACCGACGT | 7500 |

```
CCCATCAAGA AAGGGAAGAG GGAGATCAAT ATATGTAGTG TTATTCGCCC TACCTTAGGA   7560
TTAGATGTCA TCTAGCAATG TCAAATCTAG TAGAGTATAC AATGTATGGG TTCCTGGAAA   7620
CCGAGTAGAG CTTACCTGGA TTCTATGTAA ACTAAGAAAG CTCAGCAAAT ATATGCACAA   7680
ATAATTTACA GAAACAACTT GGGAATGTTG ACAAACTTGA TTATTTTTC TTTTATATAA    7740
CTAGTAATAA CGGCAAGCTC TCCGCAATCT CGTTGAGCAA AGTATAAAT GGTTACGAGC    7800
CACCTAAATA TTTTTGTTCA ACGAGATTGG AATTGGAGCT TATTATACAC AACATATACA   7860
ACAATGATTC ATCTTCTAAC TCATACAATT CTATACGTAA GGTCGAAGTT AGGAGGGAGT   7920
GAGCAACTTG GTAAAAGTA TATGGTATAA GTAAGATATT TTTAAATGTA TTATGTATCA    7980
GTTGTACTCA ATCAAAGAGC GGATAAATAC AATTGATACA ATATACAAAA TAGTTATGCA   8040
CTAAATAATA AATAGAGGAT AAAATGTAAA AGAAATACAA AATATAATTC TCTCGATCTC   8100
GCTCCCGTCT CTCCTCTCTC GATCTCACTC ATCTCTCTTC TCTTAATATG TATTCATTTT   8160
AATACAAATT AGTTCTATT TGTATTTTTT CTTCAAAATT CACGAAAAAA AATATATA     8220
AATATAAATG CATAGCGAAC AAGAATATTA TTATGAATCA TAAATAATGA AACTGTAGTT   8280
ATGGAATACT TTTAAGGGTT AATGTTGTT GTTTTGAAA TTTCCCCTCT TGAAGCCCTT     8340
AAGTGCAAAT CTTGAATCCA CTATGAATAT GATTCATTCT TTATACATAT ACAATAATAA   8400
TGATACATTT CTATTTACGA ATGATATAAT TCCCGTACAA ATAAATTTAG AGTTACAAAA   8460
GAAGATCAGC CCAGCCCATC TAATTCAAGC CTCGTGGGCC AAGAAATTTA ATGAGCTAAG   8520
GAAGGTTGGC CCTTTATTTG AAAGTGCCTA AATTGTTCAA CTCAACCTAA TTTTAGAAGG   8580
 GCCACAAACT GGGGGGGTTA GCATTTTTTT CCTTTTAAA CTTAAAGCTC TATACCATCA   8640
AGTAAATGAG ACTATTTCA AATCAAATAT GGTAACAATG GTGTTTTTC AATAACACTA     8700
ACAAAAAATT TGTATGATTA ACATGTACCT GGATACTAC ATGCCCAAGC TACATGTATA    8760
TGTTGTGATG CATTCCAAAT ATGCAAGCGA GATAAGAGCG ACCAAGATGG GTGGGAGGCG   8820
AGGGCTTGGA ATTTGTTTAT ATATCCTAGA TACATGCGAA TCCATTTGAA TGAAGTCCTT   8880
CTAGAATAAA TAGACGTATC GAAATGCACC AAAATCTAGT AAGATTTGTA ATGTTACAGC   8940
ATAACGTGCA TCTAAGTAAT TAGCTAGCTC ATACACTAGT GAGATCCTTT TAGTTACCGT   9000
ATATAAATAG TTTTGACCCA TGGGACGATC CTAACCTGTT CCCGATCAAG ACTCAAGGGC   9060
TTATAAGTCC TAATGTTGAA TGGTCTTGTA AATCCTATCA CAACCATACC CCAATACCGA   9120
GTTGGGTTGG ACCGGCTCCA TGGGCTTAGC AAACTTTGAC ATATCTACAC ATAATGGAAC   9180
AAATGAAAAA AAAAATACGA AATGAAATTA TTTTAAAAC AATAAAGACA ATATTTTTTT    9240
AGAGAAAGTT ACAAAATTAT ATACAACTTA ATATTATTAT ATCCTCTAAA AATTCCTATC   9300
TTTGAATTAA ATACAAAAAT TTCCTTTTTC CTTCTCTCTC TTTTTTCATC CGGATACATC   9360
ACTCGACCTC TATGAAATAC ACCACAATTT TGTTTGTGTA TACTAATATG GTAGAAATAT   9420
TATTACCGAT ACATAACCCC AATTATTTCA AATATAATTA TATTAGTGAT ACACAACTTA   9480
TTTATTGTTT GTTATATATA TAGAGCGAAT GAGCAATGTA TCCACAAGTT TTGAAAAATC   9540
CAAAATCATT TATTTAAAAA ACTTTTAAGA TAATGTGTAA TTAACGCCTA AAAACTATTG   9600
AGGTTTCTGT ATTCTGTATT GTATTCCTTT TAAGGAAAAA TATATAATAA CAAACTATTA   9660
ATTCAAATTA AATGTTATAT ACACAATTTG ATTTAACCTG TAGCAAAATA TTTTCATTCG   9720
CCTCTCTCCC TAGGTTTCTC ACTCGCCACT CTCGCTTTTA TACAAACACA AATGTATAAA   9780
ATGTGTTTGT GTTTGTATAA AGCGAGAGAA AATGTATATA CAAATATGAA TACATATATT   9840
TTCGTCCTAT ATACTTATAA TGATACAAAT ACAGATCTTT TCCTATCCAG TTCTCTTTTG   9900
```

|  |  |  |  |  |  |  |
|---|---|---|---|---|---|---|
| TCTTTCTCAC | TTTATACAAA | CACAAATTAT | ACAAATTACA | ATGTATAATT | ATTGTTGCAT | 9960 |
| AAAGCGAGAG | AGAGATTCGA | TATACAAATA | GTTTATTTCG | ATTCAATTAT | ATATAAATTC | 10020 |
| AAATTTTATG | CAGATATGCA | AACAAATAAA | ATAAATTTG | AGAGGCTGTC | AGCGATTTAT | 10080 |
| GCCAACGATT | TATACAAATG | ACCTACCACC | GAATTATAC | AAATCTGAAG | CATTGCCAGC | 10140 |
| GAGCTATACA | ATCTGATGCT | CCATAACAAA | CATAAAATTT | ATCATGGAAC | GTAAATATAC | 10200 |
| AAACTATGAC | TATAACATTC | AAATATAATT | TTTATGTTTG | CCATATATGA | AAATTGATCT | 10260 |
| AAGCCTTTCG | AACTATCCGA | TGTCAATAGT | TTCACCCAGA | TAGCCATTAA | TATCAAAGTT | 10320 |
| CAGGCCCAGA | TCATTGGGAT | AATTTGGGCC | TATATTGTGG | ACCGTGACTC | GAAAACACC | 10380 |
| TAATGCTACA | GGCTACACCA | AATTGATTAA | TGATTTCTCA | TCTTCTGAAA | ACAAATAAA | 10440 |
| TTTATAATTT | TTATATTACA | TAAATATTTT | TTTCCCGCTA | AATTCAAAGT | AGTCAAACAT | 10500 |
| TCAAAAATAT | TTAAACTGAT | AATCAGAGCT | CAAGTCACCT | TTTCATTTAT | ACTATTATTA | 10560 |
| TATTTTTTA | ATATTAGAGA | CAAAAAGAA | AAGCTCTCAT | ATTAAATAAT | AAAATATATA | 10620 |
| GAATTGACAG | AACCATTTGA | CCATTCTTCT | CATAGTTAAA | ATAGTATATA | ATTGGGCTCG | 10680 |
| ACTTTATATA | AAATTCTGAT | ATATTATTTA | ATATTCTTCT | TTGCTTTTCC | TTTTCTGCAT | 10740 |
| TACTTTTTTT | TTCCATTTAA | ATAATAATAC | AGGTTTATGG | GTATTATAAA | ACGGATCC | 10798 |

( 2 ) INFORMATION FOR SEQ ID NO:3:

( i ) SEQUENCE CHARACTERISTICS:
        ( A ) LENGTH: 4032 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Lycopersicon esculentum ( i x ) FEATURE:
        ( A ) NAME/KEY: precursor_RNA
        ( B ) LOCATION: 889

( x i ) SEQUENCE DESCRIPTION: SEQ ID NO:3:

|  |  |  |  |  |  |  |
|---|---|---|---|---|---|---|
| GATCAAATTT | AGTTTTGACA | TCTTCTTCAC | ATTTCAAGCA | TTAAAACCAA | TTAACACTGT | 60 |
| TTATTATTA | TTATTATATT | AATTTAAATT | TTCTGAGTTT | AATTTTATTA | TTCTAACATT | 120 |
| ATTTTATATA | CTTTTCATTG | AAAAATTGCA | TTGTTTATAT | TCTTACTTCA | TAATGTACGT | 180 |
| ATATAACATT | CTTTGCAGAC | TTCATTTATG | AAATTACACT | ATAGAATAAT | AATTTGATTT | 240 |
| ATATGTACTT | CCTTCCTTTC | AAATTGATTA | AATTGTTAAG | GTGTTTCACA | CATTTAAAAT | 300 |
| AAATTAAGTC | ACATATTAAG | CATAACTTTA | AATTTTTACA | AAAATAAGAG | CTCTCTATAA | 360 |
| AGTTTGACTT | TAAGTCTCCA | AATTTGTTAA | TACAGACCTG | AAAGAGTGTA | GGAGCTAACA | 420 |
| AAACAAATAG | TTATAAAAAG | TAATTTTATT | CAATTTTATA | GAATTAAAAG | CTATATGTGC | 480 |
| ATACACCAAA | ATTTTACATC | CTTTATCATA | GCAAATTTA | TAGAAAATAA | AAATAAATTT | 540 |
| GTAACTAATG | TTTTTTTTTT | CAAACACTGT | AAAACACGAA | AAAAATTGCT | AATGTGTAAG | 600 |
| AAAACATGTG | TAATATAAAA | CAAATATAAA | AGAGTCCACG | TGCATCGCAT | GAGTACCTAT | 660 |
| ATTAATTTTA | GCTTGAAAAT | AAAAATTAAT | ATTTTTTAT | TTCAAACACT | ACCAATTATT | 720 |
| ATAAAACTAT | TTAACTTAAT | TGGATGCACC | AACTTTGACA | GGTGTTAATT | CACTTCAATA | 780 |
| TTCAACCAAA | AAAAAAAGA | AGGTTAAAAC | GCAAAGCAAC | TTAATTCATT | TGTTATAAAT | 840 |
| TGGAGGAGCC | AAAGATAGTG | AGATTCACAA | AACTTTATAT | CTCTAAGAAT | GGAAATTCAA | 900 |

```
AAGGTATCAT AGTTTCTAAT ATTTTTTTTA ATTATATATG TCTATCTTAA GTTTCATTCA    960
TATACTCATG ATTAATTTAT TGATCATTTT AAACAATGAA ACATATCTTA GATTTAATTT   1020
TATTTATTTA TTTTTATAAC ATAGGAGTTT GATTTAACGA TAGTTCCAAC AGAAGGTGAA   1080
ATTGATGCAC CATCATCGCC AAGGAAGAAT TTATGTCTCA GTGTGATGGA ATCTGATATT   1140
AAAAATGAAA CGTCTTTTCA AGAACTCGAC ATGATTTGA CTCAATATTT AGAGACATTG    1200
TCCGAGCGAA AAAAGTATCA TATAGGTAAG GATATACATA TGTATAGTCT TTCCATACAA   1260
ACATAGTTAC TTTTTACTCA ACGAAATTAT ACAAGCATTT TAGTGATCGA GGTAATTTAA   1320
TCTCAATTTT ATTTAAATAA ATACATTTTC ATTTATTTTT ACGTGTGTAA TAAACATAAA   1380
AGTATTTATA AGAAAAATTA ATCAAAGTT ATTCATTAAT AAATCATCCC TAACTTTATT    1440
TTTACATATC TTTTAAGTAT TTTTGATTTG GCCAAATAAT ATTTTACGAT TTTATTCATA   1500
ATTATATCTT TGGTTATTTA ATTTACAGGT TATCCAATTA ACATGTGTTA CGAACATCAT   1560
GCCACTTTAG CCCCACTTTT GCAATTTCAT TTGAACAATT GTGGAGATCC CTTTACTCAG   1620
CACCCTACAG ATTTCCATTC AAAAGATTTT GAAGTGGCTG TTTTAGATTG GTTTGCACAA   1680
CTCTGGGAAA TAGAGAAAGA TGAATATTGG GGNTACATTA CTAGTGGTGG CACTNAGGGC   1740
AATCTCCATG GCCTTTTGGT TGGGCAGGTA TCATTTTCAA GAAAGGGGGT GGGGGGAGAG   1800
GTGGTAGTTT TTGAATCATA TGAAAAATCA AAAATTAAA TGGCGTAATC AGCCATTGTC    1860
ATGGTCAAAA TCATTACGAG CAAGACGTCT TACTTACTT TGTTGTACC ATAGGTACAC     1920
 AATCAATGAC AAATTTGTAT TGCCACACAA TAATGACCAC AATCCTTCTA TGCAAGAGCT  1980
ATTTCTTTCT TTTTCCCTTT GCGGTAGTTC ACAATAAACA TACCATAGTG ACGCATAAAC   2040
ATACAGTACG ATTAGCCATT TTTGCCAAAT AAAATTTATT TTCTCTCAAA CCTCCCGTAG   2100
AGGTGAGTTT TGACATATAT TATTTTTTCT CAAACCTCCT ATAGAGGTGA GTTGAGACAT   2160
ATATTCAATC CATAATGATT TTATCATATC TTGACCCATT CTCTTATAGA ATGGTCGAGC   2220
ATTCATAATA CTCATCACAA GTCACATTCT CTTCAAGGAA TTCATAAATT TGTATTATAA   2280
GTACATTGTC ATGGTTCTAA AATTCATTAT ATTTCCATGA CACACCTCAA CATCACTTTG   2340
AAAGATCAAG TGTACCATCA CTTTATCTTC TTGTCTCATG ATAGAGGATT TATAAAGTTG   2400
TCAAATTGGG TCGACAACAT TCAGAAGTCC AATGACCTTT CATACCATTT TATAATAAAA   2460
ATTCTCTTCA CATTTTGAAG GACTATTTGG AGAACCCATA GTGTTCTTCC TTTTATAATT   2520
ATCACAATGA TGACTATTAT AATTTCGTCC CTTCACGCCC TTATTCATAT CATTAATTAT   2580
TTGTCATCTT TCAGACGAAT TATTTGTTGC TACTACATTC ATATAATTGA ATGGAGCAAG   2640
TCAACAGATG GATTTCAAAG TTATCACATG TTGCTTCCAT ATTCTTTTCA AGGAATGGAG   2700
CAAATTTAAT ATGATGAATT TCAATACTTT TCATCAAAAA TATATTATTT TGCCTCAGTC   2760
ATCATCTTAT CATCAATTTG GTGCATGGAG ACTCAAACTC AATGTCTTAT CCATACAAGG   2820
CACATTAGGC CATAATTCTA TGGGACTTGA ACCCAATACC TTATCATTAT GGTGCATCAA   2880
AACTCGAATT GATGTCTTAC CCTCTTGGTG CGATAGAACT TGAATCTACC GTCTTACCCT   2940
CAAATATTTT TCATAATGAA TGACATAAAT GAGTCTTTTT TAAACAAATT TGATAACATA   3000
TTTGAGTTTT TTTCTTATGG TTAAATGATG CAAGTGCTTC ATCACTTTCA TAAAGCATTT   3060
GAACAATATT ATATATTTGT GCAGAAGAGA GCTACTTCCT AATGGATATT ATATGCATCA   3120
AAAGATTCAC ATTACTCGAT TTTCAAAGCA GCAAGAATGT ATCGAATGGA GCTACAAACT   3180
ATCAACACTT TAGTTAATGG GGAAATTGAT TATGAAGATT ACAATCAAA GTTACTTGTC    3240
AACAAGAACA AACCAGCTAT CATCAATATC AATATTGGTA AAAATACATA CATATATATT   3300
```

| | | | | | | |
|---|---|---|---|---|---|---|
| CTTACATCTT | ATAACATCAC | TTTTGGTAAA | TTAGTATATA | TGTGTTTATA | GGAACAACCT | 3360 |
| TCAAAGGAGC | TATTGATGAC | CTCGATTTCG | TCATACAAAC | ACTTGAAAAT | TGTGGTTATT | 3420 |
| CAAATGACAA | TTATTATATC | CATTGCGATG | CAGCATTATG | TGGGCTAATT | CTCCCATTTA | 3480 |
| TCAAACATGT | AAGCTTATTT | TTATTCAATT | TTCCTTCAAC | GCTCGATCGA | AGTTACAATG | 3540 |
| ACATAGTTTC | TTTCTATGGT | ATTTGACAAT | AGGCAAAAAA | AATTACCTTC | AAGAAACCAA | 3600 |
| TTGGAAGTAT | TTCAATTTCA | GGGCACAAAT | TCTTGGGATG | TCCAATGTCT | TGTGGCGTTC | 3660 |
| AGATAACAAG | GAGAAGTTAC | GTTAGCACCC | TCTCAAAAAT | TGAGTATATT | AATTCCGCAG | 3720 |
| ATGCTACAAT | TTCTGGTAGT | CGAAATGGAT | TTACACCAAT | ATTCTTATGG | TACTGTTTAA | 3780 |
| GCAAGAAAGG | ACATGCTAGA | TTGCAACAAG | ATTCCATAAC | ATGCATTGAA | AATGCTCGGT | 3840 |
| ATTTGAAAGA | TCGACTTCTT | GAAGCAGGAA | TTAGTGTTAT | GCTGAATGAT | TTTAGTATTA | 3900 |
| CTGTTGTTTT | TGAACGACCT | TGTGACCATA | AATTCATTCG | TCGTTGGAAC | TTGTGTTGCT | 3960 |
| TAAGAGGCAT | GGCACATGTT | GTAATTATGC | CAGGTATTAC | AAGAGAAACT | ATAGATAGTT | 4020 |
| TCTTCAAAGA | TC | | | | | 4032 |

( 2 ) INFORMATION FOR SEQ ID NO:4:

( i ) SEQUENCE CHARACTERISTICS:
        ( A ) LENGTH: 10965 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Lycopersicon pimpinellifolium ( i x ) FEATURE:
        ( A ) NAME/KEY: precursor_RNA
        ( B ) LOCATION: 3686..7612

( x i ) SEQUENCE DESCRIPTION: SEQ ID NO:4:

| | | | | | | |
|---|---|---|---|---|---|---|
| GATCTCGATA | AGTTATGTCT | TGTTGGAATC | GATATCAAAT | AACCGTCGAC | GGTATCTTTG | 60 |
| ATATGAGGTA | GCGCTCAATG | ATATAAATTG | TGATGAGGAT | CTTGAATTCA | AATCTGTCAT | 120 |
| ATAGTGTGAA | CAGATAAATG | GTTGGCCAAG | TAAAATGCAC | AATTCAAGTA | TATTTGTTT | 180 |
| CACTTAGAAA | AGTGACATTT | TGGACTGGTA | GTCCATAAAT | CAAGGTATAA | TGTCAGTGGG | 240 |
| GTACAAATAA | ATTATTATGT | GATAGTATAA | CCGTAAGATA | TCAAATACGG | TTTGTGCCTT | 300 |
| GGGGCATAAA | AGTTTATCGC | AAAAATCCTG | ACATTATTGG | AGATGTTTTC | TCCTTTGGTG | 360 |
| GATGCAATGA | GGTTTGTTTT | GATCTGGCAA | CATATGAAAA | ACTTGAATGC | ATGTAATGAA | 420 |
| AAATTGTAAT | GAAGGTTATA | TGAAAATCCT | TGAAACAATC | CAGGTGTCTG | AAGCATATAA | 480 |
| AGGTTGAAAG | AAACTTATCC | AATAAAGCTT | CAAGAATCCT | TATATGGATT | GAAATAGTCA | 540 |
| AGGAAGAAAA | AGGGTACAAA | AGAATGACCC | TAATTGTCCT | TGTATTTTA | TGAAAAGGTC | 600 |
| TTGGTAAGAC | AAAATTTTGT | CTTGACCTAC | AGATTGTTAA | TTTGACAAAT | AAAATATTTG | 660 |
| TCTAACAGAC | AACAGTGCAC | ATACACTGAA | AAATTTTGAT | GCAATTTTAT | GTGGATATAT | 720 |
| CGCATTCATT | GAGTACCCCA | ATGATTATGA | GATCACTTGA | CATAAATGAT | GATTCAGTTT | 780 |
| GATCTCAAAA | GAAGGATAAG | AGTTTCTTGG | TGATGAAACT | CTATCTTGGT | GCAATGAGGG | 840 |
| CACTAGTGCA | TCTTACTAAC | AATATTTGAC | TAGATATTTG | TTTTGCAGTA | AATTTACTGG | 900 |
| CAAGATTCAG | TTTCTCCCCG | ATAAAAGGAC | ATTGAAATGG | TGTTGAGCAC | ATGAATGAAT | 960 |
| ATCCTCAAAG | GACCATAGTT | ATGGGTTTAT | TCTATCCCGA | GGAATCCAAG | ACAAAATTGA | 1020 |

```
TTGATTACGC AGATGCAGAA TATTTATCTG ATCCGCATAA AGCTCTATCT CAAGCACGCT    1080
ATGTGTTTGC ATGTGGAGGC ACAATAATAT CCTGGGGATC AATGAAGCAA ATGTTGCTCT    1140
GCAGAAATAA AAGTCCTCCA TGAAGCAAGT CAAAGTGCG TCTGGTTGAG ATAAATGACA     1200
CACCATATTC AAGAAATGTG TGGTTTTTCT TTAAAAAAG AATATACCAA CCACAATGTA     1260
CAAAGATTGG AGACATCATC ACAAGAAATC AAGTGATGTT TAATCAGGG GGAGTACAAT     1320
ACGCGTTGCA CTCTTTTCC CTTGATCGAG GTTTTTTCC CACTGGATTT TCCTGACAAG      1380
GTTTTTAATG AGGCAACAAA TGGTGCGTAT CAAAGATAT GTGTACTCTT TTTCCTTCAC     1440
TAGAATTTTT TCCCACAGGG TTTTTCCTAG TAAGGTTTTA ACGAGGCACA TTATCTATGG    1500
ACATCCAAGG GGGGGTGTTA TAAATACATT GAATTAAGTG GATAGTCCAT AAGGTTGGCA    1560
CATGAACAAC CATTCATATT CACTAGGTGA CATGAACCTT TTTGGATAAG AATGTATCTA    1620
TTTATTATGA TACTTAATAT GGTAATCTTT GGAGTGATTT CTCACTCTAT AAATAGAGTT    1680
GTTCATTCAC TATTGTAATA TATACATATG AGACTTGAAT ACACTTGAAT ACGAAGAAAG    1740
TCTTATCTTC CATCTTACTT CTCTTGTCTT CTCTCTTTAT GATTATATTC TTATGAGCTT    1800
GATTTTATAA CACGAATCTC ATTATACGAA AAGTTTTACT ATTTATATTT AATTAATAGA    1860
GGATTTAAAC TTTTTAAATT TCTGTCTTTA TAGATGAGAA CTTGTCTTTT TGTTGAATCC    1920
AACTAAACAT TCAATGAAGA CAAATCAACC TGTAAATCCC TTTCAAGTAG GATTTATTCG    1980
AATCTCATTA TACGAAAAGT TTTACTATTT ATATTTAATT AATAGAGGAT TTAAACTTTT    2040
TAAATTTCTG TCTTTATAGA TGAGAACTTG TCTTTTTGTT GAATCCAACT AAACATTCAA    2100
TGAAGACAAA TCAACCTGTA AATCCCTTTC AAGTAGGATT TATTCGAATC TCATTATACG    2160
AAAAGTTTTA CTATTTATAT TTAATTAATA GAGAATTTAA ACTTTTTAAA TTTCTGTCTT    2220
TATAGATGAG AACTTGTCTT TTTGTTGAAT CCAACTAAAC ATTCAATGAA TACAAATCAA    2280
CCTGTAAATC CCTTTCAAGT AGGATTTATT CGAATCTCAT TATACGAAAA GTTTTACTAT    2340
TTATATTTAA TTAATAGAGA ATTTAAACTT TTTAAATTTC TGTCTTTATA GATGAGAACT    2400
TGTCTTTTTG TTGAATCCAA CTAAACATTC AATGAATACA AATCAACCTG TAAATCCCTT    2460
TCAAGTAGGA TTTATTCGAA TCTCATTATA CGAAAAGTTT TACTATTTAT ATTTAATTAA    2520
TAGAGAATTT AAACTTTTTA AATTTCTGTC TTTATAGATG AGAACTTGTC TTTTGTTGA     2580
ATCCAACTAA ACATTCAATG AAGACAAATC AACCTGTAAA TCCCTTTCAA GTAGGATTTA    2640
TTCGAATCTC ATTATACGAA AAGTTTTACT ATTTATATTT AATTAATAGA GAATTTAAAC    2700
TTTTTAAATT TCTGTCTTTA TAGATGAGAA CTTGTCTTTT TGTTGAATCC AACTAAACAT    2760
TCAATGAATA CAAATCAACC TGTAAATCCC TTTCAAGTAG GATTTATTCG AATCTCATTA    2820
TACGAAAAGT TTTACTATTT ATATTTAATT AATAGAGAAT TTAAACTTTT TAAATTTCTG    2880
TCTTTATAGA TGAGAACTTG TCTTTTTGTT GAATCCAACT AAACATTCAA TGAATACAAA    2940
TCAACCTGTA AATCCCTTTC AAGTAGGATT TATTCGAATC TCATTATACG AAAAGTTTTA    3000
CTATTTATAT TTAATTAATA TTCAAGTCTC AATTTTTTT TAAATATTTA CATTCCACAT    3060
TTTAATCTAT AATGAAAGTT ACTAAAATAT ACTATCAAGG AGAAAATATA CAAAATGGCC    3120
CATAACGATA GTCTTTAATA TATAATAAAT ATGTTCATTT GGATCCTTAA TATATTTCAC    3180
TTGATTAAAA TAATAATAAA TGTATAATAA AAAGTGGTCA TTTTGGTCTT TTGTCCTAAA    3240
CATAGAGTTT TTTTACCTTC AAAGAAAAAT CTTCCATAAA ATCTAATACT ATTTTTTTTT    3300
AATTTCTCCA ACAAAATTTA TTATTTTCTC TTTTAAATAT TATTTTACTG ACCTAATAAC    3360
AGTTTTTATT TTGAGCAAGA AAAGTAGTAA ATTTTGTTAA ATAAAGAACC AAAATAAATC    3420
```

```
ATTTTAATCA AAGTAAAATA TAATAACGAT TAAAATAAAG TATACATTAA GTCATTTCAA      3480

TGAAGTGAAA TAAATGAAGA AGTAAAATAA AAAAATTAAC CAAACAGTAA GCATAGTTTT      3540

GGTCATTTTC TCTAATCCCA AGTGTACCTC AAATTATAAA AGTCCTTTTG TTACTCAATT      3600

TCGTTGGTCC CAGTCATTTT CTGTGTTCAT CACCTATATA TATAGCAGTA GACTAGTAGC      3660

TTCTCCCATT CTTCTATCTT CTATTATGGC CACTCAGTGT TATGACCCCG AAAACTCCGC      3720

CTCTCGTTAC ACATTACTCC CGGATCAACC CGATTCCGGC CACCGGAAGT CCCTTAAAAT      3780

CATCTCCGGC ATTTTCCTCT CCGTTTTCCT TTTGCTTTCT GTAGCCTTCT TTCCGATCCT      3840

CAACAACCAG TCACCGGACT TGCAAATCGA CTCCCGTTCG CCGGCGCCGC CGTCAAGAGG      3900

TGTTTCTCAG GGAGTCTCCG ATAAACTTT TCGAGATGTA GCCGGTGCTA GTCACGTTTC      3960

TTATGCGTGG TCCAATGCTA TGCTTAGCTG GCAAAGAACG GCTTACCATT TCAACCTCA       4020

AAAAAATTGG ATGAACGGTA ATTAACTTTC TTATTTGAC TTTTCTTTAA TTTCTTTTTT       4080

ATTTGATCTT AAAATTGAAA TTATTATAA ATACTTATAA CAGTTCTTTT TTTTCTCAAT       4140

GATATTTATG GCTATTGATC TGTTGGGGGT ATCTTTTGGA TTCTGATTGG ATGCTATTCT      4200

GCAGATCCTA ATGGTGAGTT CAAAGTTAAT TATTATCACT ATTTTCTGCT AGTTTTTAAT      4260

TAATTATATT CTTAAACTAT GATTATAACT TTTAAAGCAA TCTCATGAAT GAGCAAATCA      4320

TTAATTCGGG TGCTTATGTA TATCATCTCG GTTAATCCTT TTACCTTATA CTCAAAACA     4380

AATATTACTC CCTTCAAAAT AATTGATGTT TGACATAATC AATGTGATGT TTAATTTTTT      4440

TTTCTTTCAA ATTTGCCCTT CCTAACCCCT ATAATGATTA TGTCAAATCC AAAGTGAAAA      4500

GACTATCATA ATTACATATG CTTTAGTCAC AATTAATTCA TGTTAAATCA TCAATAGTTT      4560

TGGATTGGAG GGAGTACTCA TTAGGAAAAA TAATTAAGCT AAATCATTCT TATTTCACT      4620

GTACATTATT TAGATTAAGG GTGAAATAGG GGAGGAATCA ATTATCTTAT TTTTCTAAAT      4680

GGACAAGTAT TTTGAAATAA CAAATTTTAA GAAAACACGT CAAGTCAAAT AGAGTAGGAT      4740

GGATGGAGTA AATTCTAACC TTTCTAGATA TTCATAAAAA TTAGTTGAAC AGACATTTTA      4800

ATAAAGACCA CAAGTTGATG AATTAAGCTT GTTGTTCCAA TATAATTGGG ATTAACATGA      4860

GATCTTGTGG CAGTAATGTT TTTTGCTTTT GTGCAATTTT CCAATAAAAA GAAAACACTT      4920

GATTGGGTCA GTATTATACA AGTTTGGAAA CCAATCACGT TATGTGGGTC ATACTTTTTT     4980

GTAGTAATGT AATAATACCA ATAGTTGGGC CCCCACTCAA AGTAATCCAT CTTCCACTTG      5040

ATTTTTTTAT TTTTTTTTTG AAATGGAGTA GGTTATCTTG GCCGCTTAGC AATTACTATT      5100

ATCATGAGTA AATGACGGAA ATTATAAATT TTTAAGATAA AATTATTATT AATCTTTTAT      5160

AATTTTATGG TTATAAAAGT CTCTCAAACT AATACAATAA TATAAGCGCT GATACATGAG      5220

TCTGATGTGC GAGATACATT AATCTGATAG GTAAAAATGA GGAACTAGAA ATTTATAAAA      5280

CTAATATGAA TAATGATAAT AAGATAACTT AAATGTGAAA TTTCTATCAT TTCTCCTAAC      5340

ATACCACTAG TGAAATTTGT TTACGTATCT TGTTGAAGAA ATCTTATCC AAAAGTCAAA      5400

AATAAAAACT CGTGGCCAAA TTTTCAAAAA AAAAGAAGG CTATCTTTTT GCCGCAAAAA       5460

GCATAGCAAT TTTGGTACGG AACGTATTGA GATTTGTAG AGTATTTAT AATTCAAATT       5520

GCATAGAAAA GTCTTACCTA TACAAGTAAA AACTTTGAAA TTTCTATTAA CGTGAATAAA      5580

TTGGTTAACA GGACCATTGT ATCACAAGGG ATGGTACCAC CTTTTTATC AATACAATCC       5640

AGATTCAGCT ATTTGGGGAA ATATCACATG GGCCATGCT GTATCCAAGG ACTTGATCCA       5700

CTGGCTCTAC TTGCCTTTTG CCATGGTTCC TGATCAATGG TATGATATTA ACGGTGTCTG      5760

GACAGGGTCC GCTACCATCC TACCCGATGG TCAGATCATG ATGCTTTATA CCGGTGACAC      5820
```

```
TGATGATTAT GTGCAAGTGC AAAATCTTGC GTACCCCGCC AACTTATCTG ATCCTCTCCT    5880
TCTAGACTGG GTCAAGTTCA AAGGCAACCC GGTTCTGGTT CCTCCACCCG GCATTGGTGT    5940
CAAGGACTTT AGAGACCCGA CTACTGCTTG GACCGGACCA CAAAATGGGC AATGGCTGTT    6000
AACAATCGGG TCTAAGATTG GTAAACGGG  TGTTGCACTT GTTTATGAAA CTTCCAACTT    6060
CACAAGCTTT AAGCTATTGG ATGGAGTGCT GCATGCGGTT CCGGGTACGG GTATGTGGGA    6120
GTGTGTGGAC TTTTACCCGG TATCTACTAA AAAAACAAAC GGGTTGGACA CATCATATAA    6180
CGGGCCGGGT GTAAAGCATG TGTTAAAAGC AAGTTTAGAT GACAATAAGC AAGATCATTA    6240
TGCTATTGGT ACGTATGACT TGGGAAAGAA CAAATGGACA CCCGATAACC CGGAATTGGA    6300
TTGTGGAATT GGGTTGAGAC TAGACTATGG GAAATATTAT GCATCAAAGA CTTTTTATGA    6360
CCCGAAGAAA GAACGAAGAG TACTGTGGGG ATGGATTGGG GAAACTGACA GTGAATCTGC    6420
TGACCTGCAG AAGGGATGGG CATCTGTACA GGTATGGACT TGGATGAACA CATTGTTTTG    6480
TTATTTTACT TTGCACCATA CACAGCGTCT AGTTGTATCG TAATAATCAT GGTAGGGAAA    6540
TTTCTTATTT AGAGAAAGTT GTTATAATCA ATGCATTTGT AGGTGAAGTA AATTCTGAAT    6600
TGTATATGAA ACGTGTCTAA TAGTGTTTCG AAATAACAGA GTATTCCAAG GACAGTGCTT    6660
 TACGACAAGA AGACAGGGAC ACATCTACTT CAGTGGCCAG TGGAAGAAAT TGAAAGCTTA    6720
AGAGTGGGTG ATCCTACTGT TAAGCAAGTC GATCTTCAAC CAGGCTCAAT TGAGCTACTC    6780
CGTGTTGACT CAGCTGCAGA GGTTTGTTGC GTTACTTTTG TTTTAAATTA CAAACACGCG    6840
CTTAATCTGC AGTCCCAAAA CTTGTTTAGC TATTGTGCAG TTGGATATAG AAGCCTCATT    6900
TGAAGTGGAC AAAGTCGCGC TTCAGGGAAT AATTGAAGCA GATCATGTAG GTTTCAGTTG    6960
CTCTACTAGT GGAGGTGCTG CTAGCAGAGG CATTTGGGA  CCATTGGTG  TCATAGTAAT    7020
TGCTGATCAA ACGCTATCTG AGCTAACGCC AGTTACTTT  TACATTCTA  AAGGAGCTGA    7080
TGGTCGTGCA GAGACTCACT TCTGTGCTGA TCAAACTAGG TTTGCTTTTC TATCTGGCAC    7140
AATTAATTTG TCCTTGTAAA ATGGAGATGG ATAAAGTAG  CGGGTTGTTG ATCTGATATA    7200
TGCAGATCCT CTGAGGCTCC GGGAGTTGGT AAACAAGTTT ATGGTAGTTC AGTACCTGTG    7260
TTGGACGGTG AAAAACATTC AATGAGATTA TTGGTAAGTG ATAATGATTC CCTTATTTTA    7320
CCTTGATTTT ATTCCATTTC TTCACTTCAC AATAATTAAA GTACTTGGCA GTTGCATTTG    7380
AGTAAAAGGT TTTTTATAAA CTGAATTTTA GGTGGATCAC TCAATTGTGG AGAGCTTTGC    7440
TCAAGGAGGA AGAACAGTCA TAACATCGCG AATTTACCCA ACAAAGGCAG TAAATGGAGC    7500
AGCACGACTC TTTGTTTTCA ACAATGCCAC AGGGGCTAGC GTTACTGCCT CCGTCAAGAT    7560
TTGGTCACTT GAGTCAGCTA ATATTCAATC CTTCCCTTTG CAAGACTTGT AATCTTCTTT    7620
ATTTCGTTTT TTTTTTCTTT TTCATTTGAA GGTTATTTCA CCGACGTCCC ATCAAGAAAG    7680
GGAAGAGGGA GATCAATATA TGTAGTGTTA TTCGCCCTAC CTTAGGATTA GATGTCATCT    7740
AGCAATGTCA AATCTAGTAG AGTATACAAT GTATGGGTTC CTGGAAACCG AGTAGAGCTT    7800
ACCTGGATTC TATGTAAACT AAGAAAGCTC AGCAAATATA TGTACAAATA ATTTACAGAA    7860
ACAACTTGGG AATGTTGACA AACTTGATTA TTTTTTCTTT TATATAACTA GTAATAACGG    7920
AAAGCTCTCC GCAATCTCGT TGAGCAAAAG TATAAATGGT TACGAGCCAC CTAAATATTT    7980
TTGTTCAACG AGATTGGAAT TGGAGCTTAT TATACACAAC ATATACAACA ATGATTCATC    8040
TTCTAACTCA TACAATTCTA TACGTAAGGT CGAAGTTAGG AGGGAGTGAG CAACTTGGTA    8100
AAAAGTATAT GGTATAAGTA AGATATTTTT AAATGTATTA TGTATCAGTT GTACTCAATC    8160
AAAGAGCGGA TAAATACAAT TGATACAATA TACAAAATAG TTATGCACTA AATAATAAAT    8220
```

```
AGAGGATAAA ATGTAAAATA AATACAAAAT ATAATTCTCT CGATCTCGCT CCCGTCTCTC      8280
CTCTCTCGAT CTCACTCATC TCTCTTCTCT TAATATGTAT TCATTTTAAT ACAAATTAGT      8340
TTCTATTTGT ATTTTTTCTT CAAAATTCAC GAAAAAAAT ATATATAAAT ATAAATGCAT       8400
AGCGAACAAG AATATTATTA TGAATCATAA ATAATGAAAC TGTAGTTATG GAATACTTTT      8460
AAGGGTTAAT GTTTGTTGTT TTTGAAATTT CCCCTCTTGA AGCCCTTAAG TGCAAATCTT      8520
GAATCCACTA TGAATATGAT TCATTCTTTA TACATATACA ATAATAATGA TACATTTCTA      8580
TTTACGAATG ATATAATTCC CGTACAAATA AATTTAGAGT TACAAAAGAA GATCAGCCCA      8640
GCCCATCTAA TTCAAGCCTC GTGGGCCAAG AAATTTAATG AGCTAAGGAA GGTTGGCCCT      8700
TTATTTGAAA GTGCCTAAAT TGTTCAACTC AACCTAATTT TAGAAGGGCC ACAAACTGGG      8760
GGGTTAGCAT TTTTTTCCTT TTTAAACTTA AAGCTCTATA CCATCAAGTA AATGAGACTA      8820
TTTTCAAATC AAATATGGTA ACAATGGTGT TTTTTCAATA ACACTAACAA AAAATTTGTA      8880
TGATTAACAT GTACCTTGGA TACTACATGC CCAAGCTACA TGTATATGTT GTGATGCATT      8940
CCAAATATGC AAGCGAGATA AGAGCGACCA AGATGGGTGG GAGGCGAGGG CTTGGAATTT      9000
 GTTTATATAT CCTAGATACA TGCGAATCCA TTTGAATGAA GTCCTTCTAG AATAAATAGA     9060
CGTATCGAAA TGCACCAAAA TCTAGTAAGA TTTGTAATGT TACAGCATAA CGTGCATCTA      9120
AGTAATTAGC TAGCTCATAC ACTAGTGAGA TCCTTTTAGT TACCGTATAT AAATAGTTTT      9180
GACCCATGGG ACGATCCTAA CCTGTTCCCG ATCAAGACTC AAGGGCTTAT AAGTCCTAAT      9240
GTTGAATGGT CTTGTAAATC CTATCACAAC CATACCCCAA TACCGAGTTG GGTTGGACCG      9300
GCTCCATGGG CTTAGCAAAC TTTGACATAT CTACACATAA TGGAACAAAT GAAAAAAAA       9360
ATACGAAATG AAATTATTTT TAAAACAATA AAGACAATAT TTTTTAGAG AAAGTTACAA.      9420
AATTATATAC AACTTAATAT TATTATATCC TCTAAAAATT CCTATCTTTG AATTAAATAC      9480
AAAAATTTCC TTTTTCCTTC TCTCTCTTTT TTCATCCGGA TACATCACTC GACCTCTATG      9540
AAATACACCA CAATTTTGTT TGTGTATACT AATATGGTAG AAATATTATT ACCGATACAT      9600
AACCCCAATT ATTTCAAATA TAATTATATT AGTGATACAC AACTTGTTTA TTGTTTGTTA      9660
TATATATAGA GCGAATGAGC AATGTATCCA CAAGTTTTGA AAAATCCAAA ATCATTTATT      9720
TAAAAAACTT TTAAGATAAT GTGTAATTAA CGCCTAAAAA CTATTGAGGT TTCTGTATTT      9780
TGTATTGTAT TCCTTTTAAG GAAAAATATA TAATAACAAA CTATTAATTC AAATTAAATG      9840
TTATATACAC AATTTGATTT AACCTGTAGC AAAATATTTT CATTCGCCTC TCTCCCTAGG      9900
TTTCTCACTC GCCACTCTCG CTTTTATACA AACACAAATG TATAAAATGT GTTTGTGTTT      9960
GTATAAAGCG AGAGAAAATG TATATACAAA TATGAATACA TATATTTTCG TCCTATATAC     10020
TTATAATGAT ACAAATACAG ATCTTTTCCT ATCCAGTTCA CTTTTGTCTT TCTCACTTTA     10080
TACAAACACA AATTATACAA ATTACAATGT ATAATTATTG TTGCATAAAG CGAGAGAGAG     10140
ATTCGATATA CAAATAGTTT ATTTCGATTC AATTATATAT AAATTCAAAT TTTATGCAGA     10200
TATGCAAACA AATAAAATAA AATTTGAGAG GCTGTCAGCG ATTTATGCCA ACGATTTATA     10260
CAAATGACCT ACCACCGAAA TTATACAAAT CTGAAGCATT GCCAGCGAGC TATACAATCT     10320
GATGCTCCAT AACAAACATA AAATTTATCA TGGAACGTAA ATATACAAAC TATAACTATA     10380
ACATTCAAAT ATAATTTTTA TGTTTGCCAT ATATAAAAAT TGATCTAAGC CTTTTGAACT     10440
ATCCGATGTC AATAGTTTCA CCCAGATAGC CATTAATATC AAAGTTCAGG CCCAGATCAT     10500
TGGGATGAAT TTGGGCCTAT ATTGTGGACC GTGACTCGAA AAACACCTAA TGCTACAGGC     10560
TACACCAAAT TGATTAATGA TTTCTCATCT TCTGAAAACA AAATAAATTT ATAATTTTTA     10620
```

```
TATTACATAA   ATATTTTTTT   CCCGCTAAAT   TCAAAGTAGT   CAAACATTCA   AAAATATTTA      10680

AACTGATGAT   CAGAGCTCAA   GTCACCTTTT   CATTTATACT   ATTATTATAT   TTTTTAATA       10740

TTAGAGACAA   AAAAGAAAAG   CTCTCATATT   AAATAATAAA   ATATATAGAA   TTGACAGAAC      10800

CATTTGACCA   TTCTTCTCAT   AGTTAAAATA   GTATATAATT   GGGCTCGACT   TTATATAAAA      10860

TTCTGATATA   TTATTTAATA   TTCTTCTTTG   CTTTTCCTTT   TCTGCATTAC   TTTTTTTTC       10920

CATTTAAATA   ATAATACAGG   TTTATGGGTA   TTATAAAACG   GATCC                       10965
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CATTCTAGAA   GATAGAGGAA   TG                                                    22
```

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
TGAAGCTTAA   TCAACCTGTA   AATCCC                                                26
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GAGCATGCTC   CGTCCTGTAG                                                         20
```

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
TTGCATGCCT   GCAGTTGTTT   GCCTCCCTGC   TG                                       32
```

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:9:

AACTGCAGAA TGGAGCAGCA CGACTC     26

INVERTASE GENE(S) AND USES THEREOF

This application is a continuation of PCT/US92/01385 filed Feb. 21, 1992, which is a continuation-in-part of U.S. patent application Ser. No. 07/771,331 to Fitzmaurice et al., filed Oct. 4, 1991, "NOVEL INVERTASE GENE(S) AND USES THEREOF", (now abandoned) which in turn is a continuation-in-part of U.S. patent application Ser. No. 07/660,344 to Fitzmaurice et al., filed Feb. 22, 1991, "NOVEL INVERTASE GENE(S) AND USES THEREOF" (now abandoned). The subject matter of U.S. patent application Ser. Nos. 07/771,331, and 07/660,344 are incorporated herein in their entirety by reference thereto.

FIELD OF THE INVENTION

The present invention is related to methods for improving the value of commercial varieties of plants by altering the phenotype of the plants and is related to the plants that exhibit the altered phenotype. In particular, this invention is related to transgenic tomato plants that have been genetically engineered to produce tomatoes that exhibit an altered solids content and an altered ratio of soluble solids to insoluble solids. Specifically, the solids content of the tomato fruit is altered by modifying the timing and level of expression of vacuolar invertase in ripening tomato fruit. This invention is also related to promoters and DNA for achieving such regulated expression in plants.

BACKGROUND OF THE INVENTION

Tomato solids include a water-soluble and a water-insoluble fraction. The insoluble solids in tomato fruit are primarily components of the cell wall and are responsible for the viscosity of processed tomato pulp. The water-soluble fraction contains the hexoses, glucose and fructose which constitute more than 90% of this fraction. Measurement of the content of these two sugars in a given fruit defines the "soluble solids content" of that fruit for commercial cultivars. The soluble solids content or ratio of soluble to insoluble solids is a major factor affecting the profitability of commercial tomato processing operations. The solids content is also important in determining the flavor and marketability of fresh market tomatoes.

The hexoses in ripened tomato fruit are produced by hydrolysis of sucrose, which is transported from the leaves, and by hydrolysis of accumulated starch, which is also derived from sucrose transported into the fruit, during fruit development. The enzyme which catalyzes the conversion of sucrose to the hexoses glucose and fructose, is beta-fructofuranosidase, commonly called invertase. Plants, including tomato, have at least two invertase activities, a soluble invertase located in the vacuole and an insoluble invertase activity bound to the cell wall.

There are characteristic differences in the activity of invertase and the distribution of sugars in plant tissues and in the fruit at different stages of ripeness. There are also differences in the activity profile of invertase and in the solids content among the fruits of different tomato species. For example, invertase activity increases in tomato fruit during ripening. Also, the fruit of *Lycopersicon pimpinellifolium*, which is a wild tomato species, is richer in invertase and expresses it earlier during ripening, and exhibits a higher soluble solids content than the cultivated tomato species, *Lycopersicon esculentum*.

Tomato growers and processors strive to develop tomato fruit that reflects the specific balance of soluble solids content and insoluble solids content desired for a particular tomato product. Traditionally, efforts to improve or alter this balance have focussed on the development of hybrid plants. For example, in an effort to increase the soluble solids content of cultivated tomatoes, such cultivated species have been crossed with wild tomato species that produce fruit with a higher soluble solids content than the cultivated varieties. The hybrid plants, however, not only acquire the desired trait but also tend to possess undesirable traits of the wild species.

There is a need, therefore, to produce improved versions of cultivated species of tomato, such as *L. esculentum*, that exhibit desirable traits of the wild species, such as a higher ratio of soluble solids to insoluble solids and a higher level of soluble solids, but that do not also have the undesirable traits of the wild species.

It would also be desirable to have the ability to produce cultivated plants that produce fruit that have a selected specific level of soluble solids content and ratio of soluble to insoluble solids content desired for a particular tomato product. In particular, it would be desirable to produce tomato fruit that have an increased soluble solids content as compared to that of presently available fruit and to thereby provide fruit that can be processed more economically.

Therefore, it is an object of this invention to provide transgenic tomato plants that express invertase earlier during ripening and express higher levels of invertase during fruit ripening than cultivated non-transgenic plants.

It is also an object of this invention to provide a means for regulating and altering the levels and ratios of soluble to insoluble solids in the fruit of cultivated tomato plants in order to select a specific level of soluble solids content and ratio of soluble to insoluble solids content desired for a particular tomato product.

It is also an object of this invention to provide tomato fruits that exhibit such soluble solids content and ratio of soluble to insoluble solids content.

SUMMARY OF THE INVENTION

Transgenic tomato plants that have fruits with solids contents and ratios of soluble to insoluble solids that differ from non-transgenic plants of the same species are provided. In particular, transgenic tomato plants that produce fruits that have improved taste and processing properties are provided.

The altered soluble solids content and ratio of soluble to insoluble solids in tomato fruit are achieved by altering the timing of expression of an invertase and level of accumulation of such invertase in the vacuoles. The timing of expression of vacuolar invertase and the level of accumulation of vacuolar invertase in the plants are altered by increasing or decreasing expression of a gene or genes encoding invertase and by changing the time during the development of the plant, particularly the fruit, that one or more of such genes is expressed.

Methods for increasing the soluble solids content of tomato fruit produced by a tomato plant by introducing DNA constructs that contain DNA encoding an invertase are provided. The DNA construct encodes an invertase that is secreted and transported to the vacuoles or is modified so that the invertase is secreted and transported to the vacuoles.

In accordance with the methods, tomato plants are transformed with the constructs, and altered levels of invertase are expressed. In particular, DNA encoding the invertase is operatively linked to a promoter recognized by the plant RNA polymerase II. If the DNA encodes an invertase that is not a vacuolar invertase, DNA encoding the invertase is operatively linked to DNA that encodes vacuolar targeting sequences, and, if necessary, DNA encoding signal sequences.

Thus, a DNA construct encoding tomato fruit invertase under the control of a promoter that is functional in plants is introduced into cells of a tomato plant, the cells containing the construct are cultured under conditions that result in the development of transgenic tomato plantlets, and the plantlets are grown into tomato plants under conditions such that the DNA encoding tomato fruit invertase is expressed.

When recombinant tomato plants containing tomato fruit invertase under the transcriptional regulation of selected control sequences are grown, both the quantity and the timing of tomato fruit invertase production can be altered. The manner in which invertase expression is altered is a function of the regulatory sequences to which the invertase-encoding DNA is operably linked. The resulting transgenic plants produce fruit that has a soluble solids content and ratio of soluble solids to insoluble solids that differ from the non-transgenic plant.

DNA constructs made by fusing tomato invertase gene sequences with homologous or heterologous regulatory sequences are also provided. In preferred embodiments, the regulatory sequences, particularly the promoter region, are selected such that the onset of expression of recombinant tomato fruit invertase commences at an earlier stage of development of the tomato fruit than would otherwise occur when the same plant does not express the recombinant invertase. In particular, DNA encoding the invertase is operably linked to a developmentally regulated promoter selected so that the onset of expression of recombinant tomato fruit invertase begins at about the breaker stage of development of tomato fruit and continues until the tomato fruit has reached the red stage. The tomato fruit of a transgenic plant that contains this DNA construct should have a soluble solids content higher than the soluble solids content of tomato fruit produced by equivalent non-recombinant tomato plants. It is preferred that the transgenic fruit have a soluble solids content at least about 0.5% higher, preferably about 1% or more, than fruit of non-modified tomato plants.

DNA constructs including regulatory regions which contain fruit-specific developmentally controlled regulatory regions are provided. These regulatory regions include promoter regions that are effective for achieving regulated expression of heterologous DNA in transgenic plants.

The preferred promoter regions include, but are not limited to, constitutive promoters, such as the CaMV 35S promoter, and developmentally regulated promoters that confer fruit specificity and appropriate temporal control on the expression of the DNA encoding invertase. Such promoters include native Lycopersicon invertase promoters. DNA encoding regulatory regions upstream from the translation start codon of the structural invertase genes in the genomic clones from L. esculentum and L. pimpinellifolium and from other developmentally regulated genes are provided.

In addition, DNA encoding proteins and sequences that direct such proteins to the vacuoles are also provided. Such DNA encodes proteins that include signal sequences and specific C-terminal precursor peptide sequences, which target or sort proteins to the vacuole. DNA encoding such targeting and signal sequences may be operatively linked to DNA encoding an invertase that lacks such sequences. In preferred embodiments, such proteins include the tomato fruit invertase signal sequence, which includes amino acids 1–47 and 48–92 of Seq. ID No. 1, and an invertase carboxyl-terminal precursor or propeptide sequence, that includes residues 607–613 of Seq. ID No. 1, preferably included as part of the last 39 amino acids of tomato invertase (amino acids 598–636 in Seq. ID No. 1) or a portion thereof that is sufficient to effect vacuolar targeting.

The constructs may be used to produce L. esculentum transgenic plants, or other transgenic plants, that express heterologous genes in a developmentally regulated manner. In particular, these constructs may be used to produce L. esculentum transgenic plants, or other transgenic plants, that express invertase under the control of the regulatory regions such that the levels of invertase expressed and the timing of expression of invertase differ from nontransgenic plants and the levels of soluble and insoluble solids in the transgenic tomato fruits differ from the fruits of nontransgenic plants.

In most preferred embodiments, DNA constructs containing the DNA encoding invertase from L. esculentum or L. pimpinellifolium operatively linked to DNA encoding the regulatory region of the invertase gene from L. pimpinellifolium or from other developmentally regulated genes that are expressed early during fruit ripening are introduced into a cultivated tomato species, such as L. esculentum, to produce transgenic plants that have an altered phenotype manifested as increased production of invertase earlier in fruit development as compared to that produced in the non-transgenic plants. Such transgenic tomato plants also can be used as a source for the production of substantially pure tomato fruit invertase and for the production of seeds that contain the heterologous DNA. Transgenic tomato plants in which the DNA encoding a mature invertase is operably linked to a secretion signal sequence, vacuolar targeting signals and to developmentally regulated promoter regions isolated from plants of the genus Lycopersicon are provided. Constructs including these signals and heterologous DNA for the purpose of producing transgenic tomato plants are also provided.

In accordance with other embodiments, transgenic plants that express lower levels of soluble solids than the non-transgenic plant and methods for decreasing the soluble solids content of tomato fruit are provided. Production of tomato fruits that have decreased soluble solids content is desirable when one seeks to obtain tomato fruit having a higher ratio of insoluble to soluble solids. Cultivars capable of producing fruit with a higher ratio of insoluble to soluble solids are of commercial value for the production of tomato products with high viscosity, such as tomato paste.

Transgenic plants that produce fruits that contain DNA constructs that result in decreased expression of invertase are provided. Reduced expression may be effected by methods such as cosuppression [for a discussion of cosuppression see Hooper, C. (1991) *J. NIH Res.* 3:49–54], by operatively linking a truncated form of a tomato fruit invertase gene to a promoter, or by expression of invertase antisense mRNA. Antisense RNA forms double-stranded RNA with the mRNA produced from the endogenous gene, thereby interfering with translation of the endogenous mRNA [see, e.g., Lichtenstein (1988) *Nature* 333:801–802]. To inhibit expression of the targeted gene, the antisense RNA can be less than full-length copy of the targeted mRNA [see, e.g., Grum et al. (1988) *Nuc. Acids Res.* 16:4569–4581 and references cited therein].

In plants that express antisense invertase mRNA or truncated forms of the protein, the amount of invertase produced in the plant, particularly during fruit development, is substantially less than the amount of invertase produced when the plant does not express antisense invertase mRNA or a truncated form of invertase. The resulting fruit should have reduced levels of the hexoses. In preferred embodiments, such reduced levels in tomato fruit can be achieved by expressing, starting at the breaker stage and continuing through the ripe stage of fruit development, an antisense copy of part, or all, of the tomato fruit invertase mRNA or a truncated form of invertase mRNA in tomato fruit. As a result, reduced amounts of invertase are produced, and sucrose, which ordinarily would have been converted to glucose and fructose, may be converted into cell wall components.

In accordance with yet another embodiment, a tomato fruit produced by a transgenic tomato plant of the genus Lycopersicon, which is derived from a transgenic tomato plantlet which contains a recombinant construct encoding antisense tomato fruit invertase mRNA, such that the total soluble solids content and ratio of soluble to insoluble solids content of the fruit is altered by virtue of the decreased conversion of sucrose into the hexoses.

In accordance with a further embodiment, methods for identifying the presence of invertase-encoding nucleic acid sequences by contacting a sample containing RNA or single-stranded DNA with a probe containing all or a least a portion of the nucleic acid sequence set forth in Seq. ID Nos. 1, 2, or 4 are provided. Hybridizing DNA that encodes all or a portion of an invertase is isolated. In instances in which such hybridizing DNA encodes a portion of the invertase, it may be used to isolate full-length clones.

In preferred embodiments, isolated, substantially pure DNA encoding vacuolar invertases that have amino acid sequences substantially identical to the vacuolar invertases of the commercial tomato species, *L. esculentum,* and the wild tomato species *L. pimpinellifolium,* are provided. Genomic DNA and cDNA clones that encode the vacuolar invertase from each species are also provided.

Protoplasts containing the DNA constructs and seeds produced by the transgenic plants that include DNA that encodes the exogenous or heterologous invertase are also provided.

In accordance with still further embodiments, methods for determining the tomato fruit invertase content of a sample; methods for identifying the presence of invertase-encoding sequences in a cDNA expression library; methods for the recombinant production of tomato fruit invertase; methods for modulating the expression of tomato fruit invertase in solanaceous plant species; and methods for targeting protein product(s) expressed from heterologous genes by recombinant plants to the vacuoles are provided.

DESCRIPTION OF THE PREFERRED EMBODIMENTS

Definitions

Unless defined otherwise, all technical and scientific terms used herein have the same meaning as is commonly understood by one of skill in the art. All publications mentioned herein are incorporated by reference thereto. All U.S. patents and publications cited herein are incorporated in their entirety by reference thereto.

As used herein, invertase refers to an enzyme that hydrolyzes sucrose to fructose and glucose and encompasses any protein that exhibits this activity in plants. The biological activity of invertase may be measured by one of several bioassays well-known in the art in which the sugars liberated by invertase activity are chemically quantified. Preferred invertases are those that, upon expression in a tomato plant, are transported through the processing pathway of the plant and targeted to the vacuoles. Tomato fruit vacuolar invertase is among those preferred herein.

As used herein, a precursor invertase refers to a protein that includes a leader or signal sequence that effects transport of the protein through plant processing pathways to yield mature protein and that includes a vacuolar targeting sequence to direct or sort the invertase to the vacuole. In the plant, signal sequences promote uptake of the protein into the endoplasmic reticulum (ER) of the plant cells.

As used herein, a signal or leader sequence, which expressions are used interchangeably, refers to a sequence of amino acids that directs transport of the translation product through the processing pathway of the host and results in the generation of a mature protein. The signal sequence includes or is modified to include one or a sequence of amino acids that is recognized by one or more host cell proteases. Such sequences may be interposed between the signal sequence and the protein, whereby, upon recognition of the processing site by the appropriate host cell protease, removal of the signal sequence may be effected. The signal sequence, processing sites and protein are referred to as a precursor protein, and the processed protein is referred to as the mature protein.

As used herein, regulatory sequences or signals also include sequences that are required for targeting proteins to selected plant organs, such as the vacuoles. Such sequences, vacuolar targeting sequences, present on the C-terminal end of the protein, effect transport of the protein to which they are linked to the vacuoles. If such sequence is absent and no other targeting sequence is present, the protein is directed to the default pathway and ultimately to the cell wall.

The processing sequences, signal sequences and targeting sequences for use herein are those that are sufficient for directing mature invertase protein to which such sequences are linked to the vacuoles of the plant host in which the invertase is expressed. Any peptide or DNA encoding such peptide that effects proper processing and vacuolar targeting in plant hosts is contemplated for use herein. The preferred processing, signal, and targeting sequences for use herein are those that effect proper secretion, processing and targeting of the *L. esculentum* vacuolar invertase. These preferred signal sequences and targeting sequences include, but are not limited to, the vacuolar invertase signal sequence and carboxyl-terminal peptide. Other such sequences that are active in plants, such as the carboxyl-terminal propeptide (CTPP) of the barley lectin proprotein, the β-1,3-glucanase CTPPs of *Nicotiana tabacum* and *N. plumbaginifolia,* may also be used. The seven amino acids near the C-terminus of tomato fruit vacuolar invertase (amino acids 607 to 613 of Seq. ID No. 1) have 86% sequence similarity to a 7-residue region of the C-terminus of β-1,3-glucanase from *Nicotiana plumbaginifolia,* which is non-homologous to invertase in the rest of its sequence.

As used herein, precursor invertase refers to unprocessed invertase that includes sequences that direct the protein through the processing pathways of the plant. Such invertase includes the signal sequences and vacuolar targeting or sorting sequences.

As used herein, exogenous invertase refers to invertase that is encoded by DNA that is introduced into the plant and is expressed in the plant in addition to endogenous invertase. The exogenous invertase may be the same as the endogenous invertase. For example, in certain embodiments, the level of invertase expressed in the plant is altered by introducing a DNA construct that encodes a Lycopersicon invertase.

As used herein, heterologous or foreign DNA and RNA are used interchangeably and refer to DNA or RNA that does not occur naturally as part of the genome in which it is present or which is found in a location or locations in the genome that differ from that in which it occurs in nature. Examples of heterologous DNA include, but are not limited to, DNA that encodes exogenous invertase and DNA that encodes RNA or proteins that mediate or alter expression of endogenous DNA by affecting transcription, translation, or other regulatable biochemical processes.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art, such as that found in Maniatis et al. [(1982) *Molecular Cloning: A Laboratory Manual,* Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. A developmentally regulated promoter is one that is turned on or off as a function of development.

As used herein, expression cassette refers to a DNA construct that includes DNA sequences that are functional for expression or encodes RNA or peptides functional for expression, and, if desired, processing and secretion of a mature protein in a selected host. Since such fragments are designed to be moved from vector to vector and into the host cell for both replication and expression, they are often referred to by those of skill in the art as "expression cassettes" or "cassettes". Accordingly an expression cassette includes DNA encoding a promoter region, a transcription terminator region, and sequences sufficient for translation, as well as any other regulatory signals, such as those that effect proper processing of the expressed protein or peptide.

As used herein, the term DNA construct embraces expression cassettes and includes DNA fragments that include more than one expression cassette.

As used herein, portions or fragments of the DNA constructs and expression cassettes are said to be operationally associated or operably or operatively linked when protein-encoding portions and regulatory regions are positioned such that expression, including transcription, translation and processing, of the protein-encoding regions is regulated by the DNA that encodes the regulatory regions.

As used herein, reference to "downstream" and "upstream" refers to location with respect to the direction of transcription from the promoter which regulates transcription of the invertase-encoding fragment.

As used herein, transgenic plants refer to plants containing heterologous or foreign DNA or plants in which the expression of a gene naturally present in the plant has been altered. Such DNA is said to be in operative linkage with plant biochemical regulatory signals and sequences. Expression may be constitutive or may be regulatable. The DNA may be integrated into a chromosome or integrated into an episomal element, such as the chloroplast, or may remain as an episomal element. In addition, any method for introduction of such DNA known to those of skill in the art may be employed.

As used herein, wild type plant refers to plants that are of the same species or are identical to the transgenic plants, but do not contain DNA or RNA that encodes the heterologous gene that may be expressed by the transgenic plant.

As used herein, homologous invertase refers to a protein that is sufficiently similar to tomato vacuolar invertase to catalyze the hydrolysis of sucrose to glucose and fructose and to so in the tomato plant.

As used herein, substantially homologous DNA refers to DNA that includes a sequence of nucleotides that is sufficiently similar to another such sequence to form stable hybrids under specified conditions. As used herein, substantially homologous DNA that encodes invertase includes DNA that hybridizes under conditions of low stringency to DNA that encodes an invertase and that encodes an invertase that functions as defined herein.

As used herein, a nucleic acid probe is a DNA or RNA fragment that includes a sufficient number of nucleotides to specifically hybridize to DNA or RNA that includes identical or closely related sequences of nucleotides. A probe may contain any number of nucleotides, from as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, two single-stranded nucleic acid segments have "substantially the same sequence," within the meaning of the present specification, if (a) both form a base-paired duplex with the same segment, and (b) the melting temperatures of the two duplexes in a solution of 0.5 X SSPE differ by less than 10° C. If the segments being compared have the same number of bases, then to have "substantially the same sequence" they will typically differ in their sequences at fewer than 1 base in 10.

As used herein, conditions under which DNA molecules form stable hybrids and are considered substantially homologous are such that the DNA molecules with at least about 60% complementarity form stable hybrids. Such DNA fragments are herein considered to be "substantially homologous". In particular, DNA that encodes invertase is substantially homologous to another DNA fragment if the DNA forms stable hybrids such that the sequences of the fragments are at least about 60% complementary and if a protein encoded by the DNA is invertase, i.e., catalyzes the conversion of sucrose into the hexoses, glucose and fructose. Thus, any nucleic acid molecule that hybridizes with nucleic acid that encodes all or sufficient portion of invertase to be used as a probe, and that encodes invertase is contemplated for use in preparing DNA constructs and transgenic tomato plants as described herein.

As used herein, breaker stage refers to the stage in fruit ripening at which the color of the fruit exhibits a definite break in color from green to tannish-yellow, pink or red, on not more than about 10% of the surface of the tomato fruit. When more than 10%, but less than about 30% of the fruit surface, in the aggregate, shows a definite change in color from green to tannish-yellow, pink, red, or a combination thereof, the fruit is said to be at the "turning" stage. When more than 30%, but less than about 60% of the fruit surface, in the aggregate, is pink or red, the fruit is said to be at the "pink" stage, which is also the 3-inch intermediate stage, of development.

As used herein, all assays and procedures, such as hybridization reactions and antibody-antigen reactions, unless otherwise specified, are conducted under conditions recognized by those of skill in the art as standard conditions.

Preparation of transgenic tomato plants.

Transgenic tomato plants that express altered levels of invertase and produce fruits that exhibit altered solids content compared to non-transgenic plants are provided. The transgenic plants contemplated herein include those in which a heterologous or foreign gene encoding invertase, encoding an antisense invertase mRNA or encoding a truncated form of invertase has been inserted into the genome or into an episomal element. By virtue of the presence of the heterologous DNA, the plant is engineered to express a desired phenotype, including an altered soluble or insoluble solids content in the fruit, or to produce a protein, which can then be isolated upon harvesting the plant.

The preferred transgenic plants provided herein are transgenic tomato plants that express DNA encoding invertase under the control of either a constitutive or a developmentally regulated promoter region that is recognized by the tomato plant transcriptional machinery, including trans acting regulatory factors and RNA polymerase II, so that expression of the invertase is either constitutive or is developmentally regulated. In addition, the DNA introduced into the plant should include sequences that insure that the invertase that is expressed in the transgenic tomato plant is processed through the plant processing pathway that directs it to the vacuoles. Consequently, the DNA encoding the invertase must also encode the necessary regulatory sequences, including a signal sequence and vacuolar targeting sequence, to target the invertase to the vacuole. Such signals and targeting sequences may be isolated as part of the DNA encoding the invertase, if the invertase is a vacuolar invertase, or the DNA encoding the regulatory sequences may be operatively linked to the DNA that encodes the invertase.

The transgenic plants that contain and express invertase that is targeted to the vacuoles can be propagated and grown to produce fruit that exhibit an altered soluble solids content, altered insoluble solids content, or altered ratio of soluble to insoluble solids compared to the soluble and insoluble solids content of tomato fruit produced by unmodified tomato plants.

Transgenic tomato plantlets (L. esculentum cv. UC82) that contain DNA constructs encoding invertase in operative linkage with a promoter recognized by the plant RNA polymerase II have been regenerated in tissue culture. Such plantlets were produced by transformation of tomato with various DNA constructs prepared herein, including constructs in which the L. esculentum histidine decarboxylase (HDC) promoter, the L. esculentum invertaase promoter, the L. pimpinellifolium invertase promoter, or the CaMV 35S promoter is fused to DNA encoding the L. esculentum tomato fruit vacuolar invertase.

The ratio of insoluble solids to soluble solids in tomato fruit may also be altered by operatively linking promoters to DNA encoding antisense or truncated forms of invertase. Expressing an antisense invertase mRNA or a truncated inactive form of invertase should result in reduced levels of the invertase gene product in the cell. Constructs that include truncated forms of invertase and that encode antisense invertase mRNA have been constructed. Such constructs have been introduced into tomato plants. These transgenic plants will be assayed for reduced expression of endogenous invertase.

Preparation of DNA constructs that encode invertase.

The DNA constructs containing DNA encoding invertase in operative linkage with regulatory sequences effective for expression and vacuolar targeting of the encoded invertase are prepared. These DNA constructs are alternatively referred to as recombinant DNA constructs, that is, fusions of various sequences, and may be produced using recombinant techniques well known in the art. The DNA constructs contain regulatory regions including promoters, transcription initiation sites, transcription termination sites, and, if necessary, vacuole sorting sequences, including signal sequences and carboxyl-terminal propeptides. Any or all of these component sequences may be homologous or heterologous to the host plant cell. Additional heterologous sequences may also be included if needed to facilitate transformation of the plant cell with the constructs or expression and proper processing and transport of the invertase.

The DNA constructs contain invertase-encoding sequences of nucleotides operably linked to genomic regulatory regions, including promoter regions. If the invertase encoded by the DNA is not directed to the vacuoles, DNA encoding appropriate regulatory sequences, such as the invertase signal and vacuolar targeting sequences, can be operably linked to the invertase coding DNA. Any sequence effective for such targeting may be used, such as, for example, the DNA encoding at least residues 607–613 of Seq. ID No. 1 and preferably residues 598–636 of Seq. ID No. 1 or a portion thereof that includes residues 607–613 and is effective for vacuolar targeting or DNA encoding any sequence of amino acids known or shown to effect vacuolar targeting. Such sequences may be empirically identified or isolated from DNA that encodes proteins known to be directed to the vacuoles.

Isolation of DNA encoding invertase.

DNA encoding an invertase may be identified using the DNA or antiserum provided herein using any method known to those of skill in the art. DNA encoding any invertase that functions in a plant host, provided that it is operatively linked to sequences that effect vacuolar targeting, is contemplated for use herein.

DNA encoding invertase may be isolated by screening a library with all or a portion of DNA encoding tomato vacuolar invertase protein, which can be employed as a probe, for the identification and isolation of invertase-encoding sequences from an appropriate cDNA or genomic library or other sample containing DNA and RNA from plant and animal species. In particular, all, or a portion sufficient to identify related DNA, of the DNA encoding invertase provided herein is used a probe to isolate related DNA fragments.

Standard hybridization or other isolation techniques, as well known by those of skill in the art, can readily be employed for such purposes. Probes employed for such purpose typically have at least 14 nucleotides. Preferred probes employed for such purpose are those of at least about 50 nucleotides in length, and may include portions from the nucleotide sequence set forth in Seq. ID Nos. 1 or 4, or the various DNA molecules which encode the amino acid sequence set forth in Seq. ID No. 1; with nucleotide sequences of about 100 nucleotides or greater being especially preferred. Examples of such especially preferred sequences are those that have sequences set forth in Seq. ID No. 1, particular from the 5' coding region and the sequences encoding and surrounding what appears to be the active site of invertase, amino acid residues 295–307, particularly residues 298–306, of Seq. I.D. No. 1.

An exemplary 5' probe would be derived from the sequence of nucleotides 316–416 as set forth in Seq. ID No. 1; while an exemplary "active site" probe would be derived from the sequence of nucleotides 880–980 as set forth in Seq. ID No. 1. For ease of detection, such probes can be labeled with radioactive, chemiluminescent, or the like, labels.

The selected hybridizing DNA fragments may be characterized in order to ascertain whether they encode a full-length protein. If they do not, they may be used as probes to isolate full-length clones. The full-length clones may then be used to express the encoded protein, which may be assayed using standard assays for invertase activity, as defined herein. Selected full-length clones that encode invertase are then assessed for the presence of DNA encoding appropriate signal and vacuolar targeting sequences by any method known to the art, including producing transgenic plants and assaying for cloned invertase in the vacuole. If such signals are absent, the selected full-length clones may be modified by operatively linking such signals.

In addition, DNA encoding invertase that is not substantially homologous to tomato fruit invertase, such as yeast invertase, may be modified by the methods herein to produce DNA encoding an invertase that is properly sorted and targeted to the vacuoles. Such modified DNA is suitable for use herein.

The cDNA provided herein has been used to obtain genomic clones and also to obtain DNA encoding invertase from a related species. DNA encoding tomato fruit vacuolar invertase has been isolated by screening *L. esculentum* cDNA expression libraries with antisera raised against vacuolar invertase purified from *L. esculentum* fruit. The isolated cDNA was used to screen *L. esculentum* and *L. pimpinellifolium* genomic DNA libraries for invertase gene promoter sequences and *L. pimpinellifolium* cDNA libraries for DNA sequences encoding *L. pimpinellifolium* vacuolar invertase. In like manner the DNA and/or antiserum provided herein may be employed to isolate DNA encoding invertases from other sources.

DNA encoding tomato fruit vacuolar invertase has also been isolated herein using polyclonal antibodies that specifically bind to purified tomato fruit vacuolar invertase. These antibodies are specifically reactive with peptide sequences of tomato fruit invertase, but are substantially unreactive with other glycoproteins or glycan-containing groups. In addition, these antibodies can be employed in a variety of methods, including methods for determining the tomato fruit invertase content of a sample. Those of skill in the art can readily determine methodologies for using antibodies to measure the tomato fruit invertase content of a sample. See, for example, Clausen (1981) *Immunochemical Techniques for the Identification and Estimation of Macromolecules*, 2nd ed., Elsevier/North-Holland Biomedical Press, Amsterdam, the Netherlands.

The DNA encoding an invertase may also be isolated by screening a cDNA library with such antibodies in order to detect translation products of cDNA clones that encode all or a part of a vacuolar invertase or by screening a cDNA or genomic library with the DNA provided herein that encodes invertase. Use of these antibodies and DNA to identify cDNAs may be accomplished using methods known to those of skill in the art [see e.g., Sambrook et al. (1989) *Molecular Cloning: A Laboratory Manual*, Vol. 2, Cold Spring Harbor Laboratory Press, Cold Spring Harbor, N.Y., pp. 12.1–12.44; Morton et al. (1987) *J. Biol. Chem.* 262: 11904–11907]. The antibodies have been used to screen a cDNA expression library and to identify DNA encoding tomato fruit vacuolar invertase. Expression libraries were prepared from poly(A)+ RNA isolated from the "pink" stage fruit of each tomato species. The libraries were screened with the antibodies made against purified tomato fruit vacuolar invertase.

Selected clones, obtained using any screening method, may, if necessary, be used to obtain full-length clones. The clones may then be tested by any manner known to those of skill in the art in order to ascertain whether the DNA encoding invertase includes sequences sufficient to direct it to the vacuoles. If such sequences are absent, DNA encoding targeting sequences may be operatively linked to the clone.

Any clone that encodes or that has been modified to encode a protein that has invertase activity as defined herein may be used for preparing DNA constructs and transferred into an appropriate host plant.

In particular, DNA encoding residues 1–636 of a tomato fruit invertase preproprotein having the amino acid sequences set forth in Seq. ID No. 1 have been isolated. In addition, genomic DNA clones encoding both *L. esculentum* and *L. pimpinellifolium* invertase (Seq. ID Nos. 2 and 4, respectively) are provided.

Those of skill in the art recognize that, by virtue of the degeneracy of the genetic code, numerous DNA molecules have nucleic acid sequences that encode the amino acid sequence set forth in Seq. ID No. 1. For example, a presently preferred nucleic acid sequence is set forth in Seq. ID No. 1, corresponding to the native nucleotide sequence encoding tomato fruit invertase from *L. esculentum*. Other sequences of nucleotides that encode this invertase or an invertase that functions equivalently may be obtained by methods known to those of skill in the art, including chemical synthesis and isolation of other invertase-encoding genes. Such invertases are limited to those that function in tomatoes and catalyze the hydrolysis of sucrose to fructose and glucose. If the invertase is not directed to the plant vacuole or is improperly processed in the tomato plant, DNA sequences encoding proper signal and vacuolar targeting sequences should be operatively linked to the invertase-encoding DNA.

Full-length cDNA and genomic clones that encode tomato fruit vacuolar invertase from both *L. esculentum* and *L. pimpinellifolium* have been isolated. The coding regions of both genes are identical. The promoter and other upstream regions of the genomic clones that encode the *L. pimpinellifolium* and *L. esculentum* invertases include repetitive regions. Each repeat unit includes the sequence 5'-TATT-TAAT-3', which matches known plant nuclear protein binding sites. The *L. pimpinellifolium* repetitive region includes an additional repeat unit and differs at two other sites from the *L. esculentum* repetitive region.

Invertase gene expression in *L. esculentum* differs significantly from that in *L. pimpinellifolium*. For example, analysis of total RNA isolated from various stages of fruit development revealed that, in *L. pimpinellifolium*, invertase mRNA appears in green fruit, and is present at high levels in pink and red fruit. In *L. esculentum* cv. UC82, however, invertase mRNA does not appear until the pink stage of fruit development and is present at high levels only in red fruit. The apparent differences in fruit solids content may result from differences in gene expression, due to cis-acting factors, including the differences in nucleotide sequences of regulatory regions associated with the invertase genes, or regulatory factors acting in trans, such as factors which induce the earlier expression of the invertase gene in *L. pimpinellifolium*.

The promoter region from the *L. pimpinellifolium* invertase gene can be fused to DNA encoding invertase and introduced into *L. esculentum* tomato plants in order to produce *L. esculentum* plants in which invertase is expressed at an earlier stage in ripening than in the non-transgenic plants. Constructs in which the promoter region from the *L. pimpinellifolium* invertase gene is fused to the *L. esculentum* invertase gene have been prepared as means for altering expression of the *L. esculentum* invertase gene and to thereby increase the soluble solids content of the fruit.

Thus, the designed pattern of expression of the invertase gene in transgenic tomato plants may be accomplished by operatively linking it to a developmentally regulated promoter. DNA encoding developmentally regulated regulatory sequences obtained from the invertase gene and sequences that direct proper secretion and targeting of invertase have been identified and isolated, and DNA constructs containing DNA encoding invertase and fruit-specific genomic regulatory sequences are provided.

Selection of developmentally regulated promoters and other regulatory sequences.

Identification and isolation of promoter regions.

To accomplish the modification of invertase gene expression in tomato plants by transformation of tomato tissue with DNA encoding invertase, such DNA has been fused to developmentally responsive promoters. Preferred promoter regions and other regulatory sequences are those that are fruit specific and developmentally controlled. Such preferred regulatory regions include those that promote expression of recombinant invertase at an earlier stage of tomato fruit development than occurs when the subject plant does not express recombinant invertase. Other embodiments include regulatory sequences that promote expression throughout fruit development.

Any developmentally regulated promoter region that, when linked to invertase-encoding DNA and introduced into a tomato plant host, does not promote expression until early in fruit ripening and promotes expression at high levels early during fruit ripening, is preferred for use herein. Especially preferred regulatory sequences are those which promote expression at about the breaker stage of tomato fruit development, the stage at which the fruit begins to turn pink or red, with continued promotion of expression until the tomato fruit has reached the red stage.

More specifically, regulatory regions have been isolated by screening a *L. pimpinellifolium* genomic DNA library with a probe containing cDNA encoding all or a portion of an invertase-encoding DNA sequence. A preferred subclone is one, as can be identified by restriction enzyme-mapping, that includes the 5' portion of an invertase-encoding sequence because there is a good chance that it will hybridize with the ATG start-site and upstream sequences of genomic clones.

For example, a 0.8-kb XhoI-HindIII 5'-end fragment of pTOM3-L1 was used as a cDNA probe and a plasmid containing an invertase-encoding fragment was isolated from an *L. pimpinellifolium* genomic DNA library. Such selected positive clones may be plaque-purified and restriction enzyme-mapped. Restriction enzyme-mapped clones having inserts extending the furthest upstream of the translation start site are then chosen for further characterization as the most likely to include the desired promoter sequences. For example, clone λPI.6, which is a preferred clone described herein, include about 4 kb upstream of the translation start site.

Developmentally regulated promoter regions may also be isolated by any method known to those of skill in the art. For example, a method for isolating clones that encode a portion of a developmentally regulated gene is described in PCT Application WO 89/12230, which is based on U.S. patent application Ser. No. 07/352,658 to Fitzmaurice et al., filed May 18, 1989, which is herein incorporated in its entirety by reference. The method provides a means to isolate promoter regions from genes that are, preferably, expressed in the tomato fruit prior to ripening, at the breaker stage. Use of this method is also described in the Examples herein. Any method by which developmentally regulated clones may be identified and isolated may be used.

The selected clones can be further characterized by northern analysis to select those that hybridize to mRNAs abundant at the developmental stage selected for study. For example, those that hybridize to mRNA that exhibits the desired developmentally regulated expression may be used as probes to screen genomic libraries in order to isolate the gene and regulatory sequences. The upstream portions can be sequenced and promoter regions identified and tested by fusing to reporter genes and looking for the appropriate regulation or pattern of expression in transgenic plants.

In particular, one such clone has been used to isolate a developmentally regulated promoter. This close, which, upon expression in vitro yields a ~50 kDa translation product, that exhibits regulated expression during fruit ripening, has been used to screen an *L. esculentum* tomato genomic library and to isolate hybridizing clones. One such clone appears to encode a protein that has substantial homology with bacterial histidine decarboxylase and is herein referred to as the HDC gene. The portion of the clone upstream from the translation initiation site has been isolated and includes the promoter region, which appears to be a developmentally regulated promoter.

One such promoter region that has been selected, herein referred to as the *L. esculentum* HDC promoter region, is among those preferred for use herein. DNA fragments that include nucleotides from about 1 to about 888 or 889 of Seq. ID No. 3, or that are substantially homologous thereto and encode a developmentally regulated promoter are herein referred to as the HDC promoter. All or a portion of this region which promotes developmentally regulated expression is operatively linked to DNA encoding invertase. Constructs including this promoter region in operative linkage with DNA encoding invertase have been prepared. The constructs, HDC/3-L1.1, HDC/3-L1.2 and HDC/3-L1.3, contain different portions of the upstream sequences and are used to prepare transgenic plants. Such transgenic plants should express developmentally regulated levels of invertase.

In other preferred embodiments, invertase gene regulatory sequences from *L. esculentum* and *L. pimpinellifolium* are provided. These have been obtained by constructing genomic libraries of each species and screening them with a probe made from an invertase-encoding clone, such as plasmid pTOM3-L1, selected from a *L. esculentum* fruit cDNA library. The positive clones have been restriction enzyme-mapped and partially or completely sequenced. Thus characterized, the regulatory regions from these DNA fragments have been used to make fusions with invertase-encoding sequences. Thus *L. pimpinellifolium* promoter sequences can be fused to *L. esculentum* invertase-encoding regions.

Other developmentally regulated promoters may be identified and isolated by means known to those of skill in the art. Such promoters preferably confer fruit specificity and an appropriate temporal control upon the expression of the coding sequences to which they are fused. For example, U.S. Pat. No. 4,943,674 to Houck et al. describes methods and examples of developmentally regulated promoter regions, such as the 2A11 promoter.

Preferred promoter regions are fruit-specific developmentally regulated promoter regions, including, but not limited to, the promoter region from *L. pimpinellifolium* and *L. esculentum*, the HDC promoter, the polygalacturonase promoter, and the 2A11 gene. Most preferred promoter regions for use herein include the HDC promoter region (Seq. ID No. 3) and the regulatory regions from the *L. pimpinellifolium* genomic clone (Seq. ID No. 4).

Invertase gene promoter regions and other developmentally regulated promoter regions may also be linked to heterologous genes for developmentally regulated expression of genes of interest in plants. The regulatory regions, including the promoters, may be linked to other genes to achieve regulated expression of such genes in plants. For example, constructs have been prepared in which different portions of the HDC promoter region and the Lycopersicon invertase promoter regions have been fused to the coding region of the *E. coli* β-glucuronidase (GUS) gene.

Finally, invertase encoding DNA may be operatively linked to a constitutive promoter, such as the CaMV 35S promoter, and introduced into a plant. DNA constructs containing the CaMV 35S promoter have been constructed and used to prepare transgenic plants. By virtue of constitutive expression of the exogenous invertase in addition to expression of the endogenous invertase gene, invertase levels in the plant should increase. The resulting transgenic fruit should exhibit increased soluble solids content.

Identification and isolation of DNA encoding processing and targeting signals.

In addition to appropriate promoter selection, other regulatory sequences, including vacuolar targeting sequences must be included in the DNA construct in order to effect proper targeting of the heterologous invertase.

The identification and isolation of regulatory elements associated with tomato fruit vacuolar invertase genes can be accomplished by use of a cDNA clone encoding invertase as a probe. In addition, such sequences may be prepared synthetically and linked to DNA encoding an invertase that lacks such sequences.

DNA encoding sequences of amino acids that direct targeting or sorting of the invertase protein, as well as other proteins, to the tomato fruit vacuoles are provided. These include signal sequences, such as the invertase signal sequence, and carboxyl-terminal propeptide sequences. A 15 amino acid glycosylated carboxyl-terminal propeptide (CTPP) of the barley lectin proprotein is necessary for the efficient sorting of this protein to plant cell vacuoles [Bednarek et al. (1990) *The Plant Cell* 2:1145–1155]. In addition, it appears that the β-1,3-glucanase CTPPs of *Nicotiana tabacum* and *N. plumbaginifolia* may also be necessary for vacuolar sorting. Sequence comparison between the Nicotiana β-1,3-glucanase CTPPs and the carboxyl-terminal domain of the vacuolar tomato fruit invertase indicates 85% sequence similarity over a region of seven amino acids between residues 607 and 613 of tomato fruit invertase-encoding regions (see Seq. ID No. 1). Vacuolar targeting sequences, thus, may include DNA that encodes residues 607–613 of Seq. ID No. 1 and any additional portions of Seq. ID No. in that region necessary to effect vacuolar targeting.

DNA encoding tomato fruit invertase signal sequences and other sequences that are removed during processing are also provided. This region of the structural gene includes nucleotides encloding amino acids 1 through about 92 of the invertase-encoding Seq. ID No. 1. This DNA, as well as DNA identified as the carboxyl-terminal sequences (including residues 607–613 of Seq. ID No. 1) of the precursor protein described above, may also be used to direct the targeting of homologous or heterologous peptides into vacuoles by host recombinant solanaceous plants. Expression of the desired homologous or heterologous peptides from DNA constructs that include the above-described signal sequences and carboxyl-terminal coding sequences upstream of, and downstream of, respectively, and in reading frame with, the peptide, should direct a substantial portion of the expressed protein into the vacuoles of the host plant. Thus, invertase-encoding genes from sources other than tomato fruit, such as yeast, may be linked to DNA encoding the CTTP and DNA encoding the signal sequence from tomato invertase, thereby directing the gene product to the vacuole.

The DNA encoding invertase and constructs herein provided may also be introduced into a variety of hosts, such as solanaceous plants, prokaryotic or eukaryotic hosts, and invertase encoded by such DNA may be expressed and isolated. Exemplary hosts include yeast, fungi, mammalian cells, insect cells, and bacterial cells. The use of such hosts for the recombinant production of heterologous genes is well known in the art. In preferred embodiments, the DNA constructs are introduced into tomato plants and expressed by transgenic tomato plants during fruit development.

Introduction of heterologous DNA into plants.

The DNA constructs provided herein are introduced into plants, plant tissues, or into plant protoplasts, particularly tomato plants, plant tissues, and protoplasts, to produce transgenic tomato plants.

Numerous methods for producing or developing transgenic plants are available to those of skill in the art. The method used is primarily a function of the species of plant. These methods include, but are not limited to, the use of vectors, such as the modified Ti plasmid system of *Agro-* bacterium tumefaciens, the Ri plasmid system of *Agrobacterium rhizogenes* and the RNA virus vector, satellite tobacco mosaic virus (STMV). Other methods include direct transfer of DNA by processes such as PEG-induced DNA uptake, microinjection, electroporation, microprojectile bombardment, and direct and chemical-induced introduction of DNA [see, e.g., Uchimiya et al. (1989) *J. Biotech.* 12:1–20 for a review of such procedures].

The resulting plants are grown, and fruits and seeds may be harvested. The transgenic plants may then be cross-bred in order to produce plants and seeds that are homozygous for the transgenic DNA. Such plants and seeds are contemplated for use herein.

The following examples are included for illustrative purposes only and are not intended to limit the scope of the invention.

EXAMPLE 1

CHARACTERIZATION OF INVERTASE PURIFIED FROM *L. ESCULENTUM* FRUIT.

A. Identification of a ~52 kDa protein as invertase.

Gel analysis of samples of invertase purified from *L. esculentum* fruit by ammonium sulfate precipitation of the supernatant of a crude homogenate followed by DEAE-cellulose, Sephacryl S-200 and Concanavalin A-Sepharose column chromatography, revealed sequential enrichment of a major protein having an apparent molecular weight of ~52 kDa and two minor species of about 30 and 24 kDa.

Polyclonal antisera reactive against carrot cell wall invertase were used to identify the ~52 kDa protein isolated from *L. esculentum* fruit as invertase. The antisera, described by Lauriere et al. [(1988) *Biochimie* 70:1483–1491], also reacted with the ~30 and ~24 kDa proteins.

The predominant ~52 kDa protein present in purified preparations of *L. esculentum* fruit vacuolar invertase, as well as the two minor additional proteins (~30 and ~24 kDa) detected in these preparations, were subjected to N-terminal protein sequence analysis. The ~52 kDa protein and the ~24 kDa protein contain identical residues at the N-terminus (22 residues); the ~30 kDa protein yielded a 22-amino acid sequence that was different from the sequence of N-terminal residues obtained from the ~52 and ~24 kDa proteins. Subsequent analysis of the amino acid sequence deduced from a full-length invertase cDNA clone pTOM3-L1 (Example 2B) confirmed that the 22-residue sequence representing the N-terminus of the ~30 kDa protein is contained within the intact ~52 kDa protein.

Analysis of purified *L. esculentum* invertase showed that the ~52 kDa protein hydrolyzed sucrose to glucose and fructose and that it hydrolyzed raffinose to melibiose and fructose.

Invertase activity and substrate specificity were assayed by reacting 3.8 µg of protein obtained following Concanavalin A-Sepharose column chromatography with 90 mg/ml of substrate (sucrose or raffinose), in 13.6 mM citric acid and 26.4 mM NaHPO$_4$ (pH 4.8) at 30° C. for 30 minutes. The reaction was stopped with the alkaline copper reagent of Somogyi [(1945) *J. Biol. Chem.* 160:51–68] and the liberated reducing sugars were measured according to Nelson [(1944) *J. Biol. Chem.* 153:375–380]. To analyze substrate activity, the products of these reactions were subjected to thin layer paper chromatography using isobutanol:pyridine:H$_2$O: acetic acid (12:6:4:1) as the solvent for ascending chromatography [Gordon et al. (1962) *J. Chromatog.* 8:44].

The positions of the carbohydrates were detected with alkaline silver nitrate [Chaplin (1986) "Monosaccharides", in *Carbohydrate Analysis, A Practical Approach*, Chaplin and Kennedy, eds; IRL Press, Washington, DC, pp. 1–36].

This characterization, in addition to the invertase activity assay results and the cross-reactivity to carrot invertase antibody, and protein sequence analysis confirmed identification of the ~52 kDa protein as *L. esculentum* invertase.

B. Identification of ~52 kDa protein as vacuolar invertase

Invertase activities in protoplasts and vacuoles were evaluated and the purified invertase protein was compared to vacuolar proteins.

Protoplasts and vacuoles were purified from *L. esculentum* fruit tissue by squeezing two ripened tomato fruit into 35 ml of 25 mM Tris-MES [2-(N-morpholino)ethanesulfonic acid], pH 6.5, containing 0.7M mannitol [Low pH Buffer; Boudet and Alibert (1987) *Methods in Enzymology* 148:74–81] and filtering the resulting suspension through two pieces of cheese cloth and stainless steel mesh (30 mesh). The filtrate was centrifuged at 100× g for 3 min to collect protoplasts. The protoplasts were then resuspended in the same buffer and collected by centrifugation at 100× g for 3 min.

Vacuolar fractionation was accomplished by a modification of the procedure described by Boudet and Alibert (1987) *Methods in Enzymology* 148:74–81. The protoplast fraction was diluted 1:4 with 20% (w/v) Ficoll in Low pH Buffer, then overlaid with 5 ml of Low pH Buffer containing 6 mg/ml DEAE-dextran and 10% (v/v) Ficoll, 2 ml of 6 mg/ml dextran sulfate (potassium salt) and 5% (v/v) Ficoll in 25 mM Tris-MES, pH 8.0, containing 0.7M mannitol (High pH Buffer), and 2 ml of 1.2 mg/ml dextran sulfate and 1% (v/v) Ficoll in High pH Buffer followed by centrifugation at 2000× g for 30 min. Vacuoles were recovered from the interface between the 5% and 1% Ficoll layers.

Protoplasts and vacuoles were lysed in the presence of invertase assay buffer and analyzed for invertase activity, as described above. The results of invertase assays of vacuolar and protoplast lysates revealed that the invertase activity in the vacuolar fraction was ~16-fold higher than the invertase activity in the protoplasts.

To determine if the vacuolar form of invertase was the form of invertase purified from *L. esculentum* fruit tissue, total protein from the purified vacuoles was subjected to SDS-PAGE and subsequent immunoblot analysis with the carrot invertase-specific antisera. The ~52 kDa, ~30 kDa, and ~24 kDa proteins detected in invertase purified from tomato fruit were detected in the vacuolar proteins.

C. Production of polyclonal antisera to *L. Esculentum* vacuolar invertase.

Polyacrylamide gel-purified *L. esculentum* fruit vacuolar invertase (~52 kDa species obtained following separation on Concanavalin A-Sepharose) was excised from a gel, and 75 to 100 µg of protein were injected into rabbits, three times at intervals of two weeks, for the production of antibodies. The immunoglobulin fraction from immunized rabbits was subsequently purified from raw antiserum by Protein A-Sepharose affinity column chromatography. To remove antibodies reactive with glycans, the immunoglobulin fraction of this antiserum was passed over a horseradish peroxidase-Sepharose column which was prepared by coupling horseradish peroxidase to CNBr-activated Sepharose 4B (Pharmacia LKB Biotechnology, Piscataway, N.J.).

The antibodies reactive with tomato fruit invertase peptides did not bind to the column and the resulting "cleared" antibody fraction reacted specifically with tomato fruit invertase.

EXAMPLE 2

ISOLATION OF cDNA ENCODING *L. ESCULENTUM* VACUOLAR INVERTASE.

A. Library construction.

Total RNA was isolated from fresh *L. esculentum* cv. UC82 (grown from seeds obtained from Dr. Charles Rick, University of California at Davis, Dept. of Vegetable Crops) 3-inch intermediate fruit (i.e., fruit at the "turning" to "pink" stage of development) as described by De Vries et al. [(1988) In *Plant Molecular Biology Manual,* S.B. Gelvin, R.A. Schilperoot, and D.P.S. Verma, eds., Kluwer Academic Publishers, Dordrecht, The Netherlands, pp. B6:1–13]. Poly(A)$^+$RNA was isolated from total RNA by oligo(dT)-cellulose chromatography (mRNA Purification Kit, Pharmacia LKB Biotechnology, Piscataway, N.J.).

The poly(A)$^+$RNA was used to construct size-selected cDNA libraries (of ~0.6–2 kb and ~2–4 kb and greater) in λgt11. cDNA synthesis was carried out by the method of Lapeyre and Amalric [(1985) Gene 37:215–220] with the following modifications. A NotI-oligo(dT) primer-adapter (Promega Corporation, Madison, Wis.) was used in first-strand synthesis. The addition of EcoRI adapters was followed by digestion with NotI, generating cDNA inserts with a NotI site at the polyadenylated end and an EcoRI site at the opposite end. The cDNA was size-fractionated on a Sepharose CL-4B column. cDNAs of approximately 0.6–2 kb and 1.2–4 kb or greater in length were ligated into λgt11 Sfi-Not (Promega Corporation, Madison, Wis.) which had been digested with EcoRI and NotI. The cDNA-containing λgt11 vectors were then packaged and amplified (Gigapack$^R$ II Gold Packaging Kit, Stratagene Cloning Systems, La Jolla, Calif.).

B. Library screening.

To identify clones expressing tomato invertase, the immunological screening protocol described in Sambrook et al. [(1989) *Molecular Cloning: A Laboratory Manual,* Vol. 2, Cold Spring Harbor Laboratory Press, Cold Spring Harbor, N.Y., pp. 12.16–12.20] was used to screen directionally cloned *L. esculentum* fruit cDNA expression libraries. The primary antibody was antisera raised against tomato invertase protein and cleared of anti-glycan antibodies (see Example 1), and was pretreated as follows: 250 μl each of *E. coli* strain Y1090 extract and crude λgt11-*E. coli* strain Y1090 lysate were added to 5 ml of a 1:10 dilution of the tomato invertase antisera in the blocking buffer (described in the screening protocol), and the mixture was incubated 4 h at room temperature, then diluted 1:100 in blocking buffer. The secondary antibody was an anti-rabbit IgG-alkaline phosphatase (AP) conjugate (Promega Corporation, Madison, Wis.), diluted 1:7500 as described in the screening protocol.

Approximately 250 immunopositive plaques were detected in the primary screen of approximately 300,000 plaques. Six positive clones were plaque-purified by standard methods. The inserts of three of these clones, ranging from ~1.1 to 1.5 kb in size, were subcloned into the SfiI and NotI sites of vector pGEM-11Zf(−) (Promega Corporation, Madison, Wis.). Plasmid mini-preps were performed according to the protocol of Sambrook et al. [(1989) *Molecular Cloning: A Laboratory Manual,* Vol. 1, Cold Spring Harbor Laboratory Press, Cold Spring Harbor, N.Y., p. 1.40].

The insert DNAs were sequenced according to the USB Sequenase$^R$ (United States Biochemical Corporation, Cleveland, Ohio) protocol. The complete sequence of the longest of the clones, pTOM3, contains 1339 bp which correspond to bases 840–2163 in Seq. ID No. 1, plus a poly(A) tail which has 15 adenine residues. Several classes of cDNA clones were identified, based on the location of the poly(A) tail.

Comparison of the deduced amino acid sequence of the insert in pTOM3 and the amino acid sequences of peptides generated by CNBr cleavage of the gel-purified preparation of *L. esculentum* vacuolar invertase revealed that a portion of the deduced amino acid sequence is present in one of the sequenced peptides.

The N-terminal protein sequence determined by sequencing the predominant ~52 kDa protein of partially purified preparations of *L. esculentum* fruit vacuolar invertase was not located in the pTOM3-deduced amino acid sequence, indicating that this cDNA clone does not encode a full-length invertase mRNA.

A 0.5 kb HindIII fragment of pTOM3, containing the 5' half of the DNA insert, was used as a probe to rescreen both the large insert (approximately 1.2 up to >4 kb) and small insert (~0.6–2.0 kb) λgt11 *L. esculentum* cv. UC82 fruit cDNA expression libraries for full-length invertase cDNA clones, essentially according to the procedure of Maniatis et al. [(1982) *Molecular Cloning: A Laboratory Manual,* Cold Spring Harbor Laboratory Press, Cold Spring Harbor, N.Y., pp. 320–321, 326–328]. The filters were washed for 15 min each, once at 42° C. in 2× SSC, 0.1% SDS, once at 42° C. in 1× SSC, 0.% SDS, once at 42° C. in 0.5× SSC, 0.1% SDS, and once at 65° C. in 0.1× SSC, 0.1 % SDS.

Eleven hybridizing clones were plaque purified. The insert sizes of these clones ranged from ~1.4 to ~2.2 kb. Inserts from several of these clones were subcloned and sequenced as described above. The longest clone, pTOM3-L1, is 2199 bp in length (see, Seq. ID No. 1), encodes full-length tomato invertase, and also contains an additional 21 bp relative to pTOM3 preceding the poly (A) tail.

Comparison of the 3' ends of all of the *L. esculentum* cDNA clones sequenced revealed five classes of clones, based on the location of the poly(A) tail, at either the site indicated in Seq. ID No. 1, or a relative position of −23, −21, −17, or +13. All overlapping sequences were identical, except at a site 37 bp upstream of the beginning of the poly(A) tail in pTOM3-L1. That site contains a pyrimidine in all cases, C in 8 of 9 clones and T in the other clone.

Comparison of the amino acid sequence deduced from pTOM3-L1 with the amino acid sequences of peptides generated by CNBr cleavage of vacuolar invertase purified from *L. esculentum* fruit and the amino-terminal sequence of purified invertase indicated that the protein encoded by this protein is invertase. In addition, sequence analysis of the ~30 kDa and ~24 kDa proteins which reacted strongly with anti-carrot invertase antisera in immunoblots of purified *L. esculentum* vacuolar invertase suggests that these proteins are degradation products of the mature invertase protein. The first 22 amino acids of the ~24 kDa protein were determined by sequence analysis to be identical to the first 22 amino acids of the ~52 kDa protein. The first 22 amino acids of the ~30 kDa protein were determined by sequence analysis and did not correspond to the amino terminus of *L. esculentum* fruit vacuolar invertase. The first 22 amino acids of the ~30 kDa putative degradation product of tomato invertase are identical to amino acids 253–274 deduced from the nucleotide sequence of pTOM3-L1 (Seq. ID No. 1).

The ATG translation start signal of pTOM3-L1 is the only in-frame ATG that results in an open reading frame from which a single peptide including all of the amino acid sequences derived from purified *L. esculentum* fruit vacuolar invertase can be deduced. Amino terminal sequence analysis of purified *L. esculentum* fruit vacuolar invertase indicates that the mature protein begins at the tyrosine residue at position 93 relative to the methionine encoded by the translation start codon (Seq. ID No. 1). Therefore, it appears that the first 92 amino acids of the protein encoded by pTOM3-L1 are co- or post-translationally cleaved, leaving a sequence of 544 amino acids extending from the amino terminus of the mature protein to the residue encoded by the codon preceding the stop codon.

Computer-assisted analysis of the resulting 544 amino acid peptide indicates that it has a molecular weight of ~60 kDa. The molecular weight of the mature deglycosylated tomato fruit vacuolar invertase was estimated to be ~45 kDa by SDS-PAGE. It is possible that additional post-translational modifications of the 636 amino acid precursor protein occur at the carboxyl terminus.

Based upon the assumption that the molecular weight of the mature protein is ~45 kDa, the carboxyl terminus of the mature protein has been predicted to be at amino acid position 502. This prediction is based upon the apparent molecular weight of the mature protein estimated by SDS-PAGE and thus is subject to experimental error of ±10 amino acids.

EXAMPLE 3

ISOLATION OF A cDNA ENCODING *L. PIMPINELLIFOLIUN* VACUOLAR INVERTASE.

A cDNA expression library was prepared from orange fruit of *L. pimpinellifolium* Trujillo, La Libertad Perù (grown from seeds obtained from Dr. Charles Rick, University of California at Davis, Dept. of Vegetable Crops) and was screened essentially as described in Example 2, except that the initial screen used $^{32}$P-labeled *L. esculentum* cDNA clone pTOM3 as a probe. Five clones were identified, plaque purified, subcloned, and sequenced. The longest clone (pLP-19) contained an insert which is 30 bp shorter than the pTOM3-L1 insert at the 5' end and 7 bp longer at the 3' end prior to the poly(A) tail.

To isolate a full-length cDNA clone that encodes *L. pimpinellifolium* invertase, the *L. pimpinellifolium* fruit cDNA expression library was re-screened using a $^{32}$P-labeled synthetic oligonucleotide complementary to nucleotides 7–33 of the *L. esculentum* cDNA (see Seq. ID NO. 1). Hybridization was carried out overnight at 42° C. in 50% formamide, 5× SSPE, 5× Denhardt's solution, 0.1% SDS, 200 μg/ml denatured salmon sperm DNA and 10$^6$ cpm/ml radiolabeled probe. Several of the hybridizing clones were purified and characterized and compared with cDNA pTOM3-L1. *L. pimpinellifolium* clone pPIM11 was determined to be a full-length invertase-encoding cDNA that contains 7 nucleotides at the 5' end that are not present at the 5' end of pTOM3-L1 and 17 fewer nucleotides preceding the poly(A) tail than pTOM3-L1. Clone pPIM11 extends seven nucleotides farther in the 5' untranslated sequence direction than pTOM3-L1; the overlapping portions of the 5' ends of pPIM11 and pTOM3-L1 are identical.

The nucleotide sequences of the *L. pimpinellifolium* cDNA clones are essentially identical to those of the *L. esculentum* cDNA clones, differing only slightly at the 3' end. Several classes of *L. pimpinellifolium* cDNA clones with 3' ends of differing lengths were identified, as was the case for the *L. esculentum* clones. The *L. pimpinellifolium* cDNA poly(A) tails begin either at the same site as in *L. esculentum* clone pTOM3-L1 (see, Seq. ID No. 1) or at a relative position of −21, −17, or +7, and overlapping regions are identical in all clones. The site comparable to the variable site 37 bp upstream of the pTOM3-L1 poly(A) tail also contains a pyrimidine in all the *L. pimpinellifolium* cDNA clones, except that it is a T in 6 of the 7 clones sequenced and a C in only one clone. No other differences were found between the vacuolar invertase cDNAs of the two species.

EXAMPLE 4

ISOLATION OF *L. PIMPINELLIFOLIUM* VACUOLAR INVERTASE GENE PROMOTER REGIONS.

A. Construction of a genomic library.

Genomic DNA was isolated from seedling tissue of *L. pimpinellifolium* Trujillo, LaLibertad Perù (grown from seeds obtained from Dr. Charles Rick, University of California at Davis, Dept. of Vegetable Crops) according to the procedure of Rogers and Bendich [(1988) *Plant Molecular Biology Manual*, pp. A6/1–10, Kluwer Academic Publishers, S. B. Gelvin, R. A. Schilperoot, eds.]. Restriction enzyme fragments generated by partial digestion with Sau3AI were cloned into λFIX™ II (Stratagene, La Jolla, Calif.) according to manufacturer's instructions. The ligation reaction was packaged using Stratagene Gigapack™ II Gold packaging extracts.

B. Library screening.

A 0.8 kb XhoI-HindIII restriction enzyme fragment from plasmid pTOM3-L1 (a clone encoding invertase from the *L. esculentum* fruit cDNA library), see Example 2B, was labeled with $^{32}$P. This probe was used to screen the *L. pimpinellifolium* genomic library as described in Example 2, except that the wash in 0.5× SSC, 0.1% SDS was omitted. Two of the 12 positive clones, λPI.1 and λPI.3, were selected for further characterization.

The *L. pimpinellifolium* genomic library was then rescreened by the method described above with the $^{32}$P-labeled, gel-purified ~0.8 kb XhoI-HindIII fragment from the 5' end of the pTOM3-L1 insert. Six positive clones were selected for further characterization. Clone λPI.6 was determined to encode the largest amount of sequence 5' from the initiation ATG.

C. DNA sequencing.

Restriction enzyme fragments of the insert of λPI.6 were subcloned and sequenced by the dideoxynucleotide chain termination method, using Sequenase® (United States Biochemical Corporation, Cleveland, Ohio). The sequenced region, provided in Seq. ID No. 4, includes the promoter and protein-encoding regions of the *L. pimpinellifolium* tomato vacuolar invertase gene.

The *L. pimpinellifolium* genomic sequence including the promoter and protein-encoding regions is set forth in Seq. ID No. 4. The transcription start site was identified by primer extension analysis by the method of Sambrook et al. [(1989) *Molecular Cloning: A Laboratory Manual*, Cold Spring Harbor Laboratory Press, Cold Spring Harbor, N.Y., Vol. 1, pp. 7.79–7.83]. The oligonucleotide primer used in the primer extension reaction is complementary to nucleotides 74–107 of SEQ ID No. 1.

The transcription start site is located at nucleotide position 3668 of Seq. ID No. 4. The TATA box appears to be located at nucleotide positions 3637 through 3640. The translation start site appears to begin at nucleotide position 3686, and the stop codon begins at nucleotide position 7609. In addition, the cDNA 3' end sequences of different lengths share 100% sequence identity with the comparable regions of the genomic sequence. The variable site located near the 3' end of the cDNAs contains a T in the genomic clones sequenced.

EXAMPLE 5

ISOLATION OF *L. ESCULENTUM* INVERTASE GENE PROMOTER REGIONS.

A. Construction of genomic library.

A genomic library was constructed in λ FIX™ II using DNA isolated from seedling tissue of *L. esculentum* cv. UC82 (grown from seeds obtained from Hunt-Wesson Foods, Inc., Pasadena, Calif.), according to the procedure described in Example 4.

B. Library screening.

The insert of plasmid pTOM3 (see Example 2) was labeled with $^{32}$P and used as a probe to screen the *L. esculentum* genomic library as described in Example 4. Four clones containing putative invertase-encoding sequences were identified, and three were selected for further characterization.

C. DNA sequencing.

Restriction fragments of the insert of the above genomic clones were subcloned and sequenced. The sequenced regions, provided in seq. ID No. 2, include the promoter and protein-encoding regions of *L. esculentum* tomato vacuolar invertase gene.

The *L. esculentum* genomic sequence including the promoter and protein-encoding regions is set forth in Seq. ID No. 2. The transcription start site is located at nucleotide position 3502. The TATA box appears to be located at nucleotide positions 3471 through 3474. The translation start site appears to begin at nucleotide position 3520, and the stop codon begins at nucleotide position 7443. The cDNA 3' end sequences of different lengths share 100% identity with the comparable region of the genomic sequence. The variable site located near the 3' end of the cDNAs contains a C in the genomic clones sequenced.

EXAMPLE 6

PREPARATION OF CONSTRUCTS CONTAINING TOMATO INVERTASE GENE PROMOTERS AND/OR CODING REGIONS.

A. *L. pimpinellifolium* invertase promoter/invertase gene constructs.

Plasmid PI.6/BIN was constructed by inserting DNA containing regulatory and protein-encoding regions of the *L. pimpinellifolium* invertase gene into pBIN19 [Bevan (1984) *Nucl. Acids Res.* 12:8711–8721; Clontech, Palo Alto, Calif.], a vector containing DNA sequences required for transferring DNA to plant cells. PI.6/BIN contains the *L. pimpinellifolium* invertase gene coding region as well as 3.7 kb of upstream and 3.4 kb of downstream sequence (nucleotides 1–10965 in Seq. ID No. 4).

Plasmid PI.6/BIN was constructed in two steps: (1) the ~7.8 kb insert DNA purified from plasmid pPI.6B7.8, which includes part of the *L. pimpinellifolium* invertase gene and ligated with BamHI-digested plasmid, pPI.6BgB2.9, which includes the remainder of the invertase gene, to yield a third plasmid; and (2) the ~10.7 kb insert, which includes nucleotides 1–10965 of Seq. ID No. 4 and 18 additional nucleotides (EcoRI, SalI, XhoI polylinker) at the 5' end, was purified from an EcoRI/BamHI (partial) digest of the plasmid and ligated with EcoRI- and BamHI-digested pBIN19 (Clontech, Palo Alto, Calif.) to yield PI.6/BIN.

B. *L. esculentum* invertase promoter/invertase gene constructs.

Plasmid pEI.23/BIN was constructed by inserting DNA containing regulatory and protein-encoding regions of the *L. esculentum* invertase gene into pBIN19. Plasmid pEI.23/BIN contains the *L. esculentum* invertase gene coding region as well as 3.5 kb of upstream and 3.4 kb of downstream sequences (nucleotides 1–10798 in Seq. ID No. 2).

Plasmid pEI.23/BIN was constructed in two steps: (1) a ~7.8 kb BamHI insert was purified from a plasmid, pEI.3B7.8, which includes a portion of the the *L. esculentum* invertase gene and then ligated to a BamHI-digested plasmid, pEI.2BB2, which contains the remainder of the gene, to produce a third plasmid, pEI.23BgB10.7, from which the ~10.7 kb insert was purified from an EcoRI/BamHI (partial) digest of the plasmid; and (2) the purified fragment (nucleotides 1–10798 in Seq. ID No. 2 with the polylinker at the 5' end), was ligated to EcoRI- and BamHI-digested pBIN19 to yield pEI.23/BIN.

C. *L. esculentum* invertase promoter/GUS gene constructs.

DNA from the promoter region of the *L. esculentum* gene between 3 base pairs and either 747, 913, or 1079 base pairs upstream from the initiator ATG from pEI.23BgB10.7 (Example 6B) corresponding to sequences between nucleotides 3517 and either 2773, 2607, and 2441 in Seq. ID No. 2 was amplified by the polymerase chain reaction (PCR) using Seq. ID No. 5 as a first oligonucleotide primer, which created an XbaI site 1 bp upstream of the initiator ATG, and Seq. ID No. 6 as a second primer (located in the region of direct repeats), which created a HindIII site 752 bp, 918 bp, 1084 bp and possibly additional sites upstream of the initiator ATG. These multiple priming sites are due to the presence of six 166-bp tandem direct repeats in this promoter.

The PCR products were digested with HindIII and XbaI and ligated with HindIII- and XbaI-digested pBI221 (Clontech, Palo Alto, Calif.) to fuse the promoter sequences with the GUS gene coding sequence in pBI221. Two correct plasmids, EI2GUS715 and EI2GUS1100, were identified by the production of ~750 bp and ~1100 bp fragments, respectively, upon digestion with HindIII and XbaI.

Plasmid EI2GUS715 was digested with EcoRI and HindIII, and the 3.1 kb fragment was ligated with EcoRI- and HindIII-digested pBIN19 to produce EI2GUS715BIN.

The 3.4 kb EcoRI-HindIII fragment of plasmid EI2GUS1100 was ligated into pBIN19 by the same procedure used for EI2GUS715 to produce plasmid EI2GUS1100BIN.

EXAMPLE 7

TRANSFORMATION OF TOMATO PLANTS WITH INVERTASE PROMOTER CONSTRUCTS.

A. Transformation of *L. esculentum* seedlings.

The transformation of seedlings of *L. esculentum* cv. UC82 (grown from seeds obtained from Ferry Morse Seed Co., Modesto, Calif.) was done essentially according to the protocol of Fillatti et al. [(1987) Bio/Technology 5:726–730]. Plasmids PI.6/BIN and EI.23/BIN (Example 6) were inserted into *Agrobacterium tumefaciens* strain LBA4404 [Clontech, Palo Alto, Calif.] through triparental mating [Ditta, G. (1986) *Meth. Enzymol.* 118] for transfer into *L. esculentum* seedlings.

The cultures were incubated at 27° C. with 16 hours of light per day under 4,000 lux of light intensity. When kanamycin-resistant shoots reached a height of one inch, they were rooted on rooting medium, which is identical to regeneration 2 Z medium except that it lacks hormones and contains 250 μg/ml cefotaxime and 50 μg/ml kanamycin. The transgenic shoots are grown into fruit-bearing transgenic tomato plants.

B. Assays for recombinant gene expression.

Tomato fruit tissues are assayed for invertase or GUS expression at various stages of fruit development. Invertase activity is determined according to the assay described in Example 1. GUS activity is determined essentially according to the protocol of Jefferson [(1987) *Plant Mol. Biol. Rep.* 5:387–405]. Protein concentration is determined according to the Protein Assay using reagents obtained from Bio-Rad Laboratories (Richmond, Calif.).

EXAMPLE 8

CONSTRUCTION OF HDC PROMOTER CONSTRUCTS

A. Isolation of a developmentally regulated gene.

1. Construction of cDNA library.

Tomato fruit at the 3-inch intermediate stage was collected from greenhouse-grown *L. esculentum* cv. UC82 (grown from seeds obtained from Hunt-Wesson Foods, Fullerton, Calif.) and frozen in liquid nitrogen. Polysomes were prepared from 10 g of pulverized frozen tissue [Schroder et al. (1976) *Eur. J. Biochem.* 67:527–541] and RNA was extracted from the polysomes using an SDS-phenolchloroform procedure similar to that described by Palmiter [(1974) *Biochemistry* 13:3606–3615] and stored at −70° C. Poly(A)+RNA was selected by affinity chromatography on oligo(dT)-cellulose columns using the procedure of Aviv and Leder [(1972) *Proc. Natl. Acad. Sci. USA* 69:1408–1412], except that LiCl was used instead of NaCl.

A cDNA library was prepared by methods similar to those reported by Villa-Komaroff et al. [(1978) *Proc. Natl. Aced. Sci. USA* 75:3727–3731]. The cDNA molecules were made double-stranded with DNA polymerase I, Klenow fragment (New England BioLabs, Beverly, Mass.). To insure completion of the second strand synthesis, the DNA molecules were incubated with reverse transcriptase (Molecular Genetic Resources, Tampa, Fla.). The doublestranded molecules were made blunt-ended by digestion with S1 nuclease (Boehringer Mannheim Biochemicals, Indianapolis, Ind.) and tailed with d(C) using terminal transferase (Ratliff Biochemicals, Los Alamos, N. Mex.).

The tailed DNAs were annealed to pBR322 DNA which had been digested at the PstI site and tailed with d(G) (New England Nuclear, Boston, Mass.). The recombinant plasmid DNA molecules were used to transform LE392 *E. coli* cells which were then plated on LB-tetracycline (15 μg/ml) plates. The resultant cDNA library was stored by the procedure of Hanahan and Meselson [(1980) *Gene* 10:63–67].

2. Library screening.

The cDNA library was screened to identify clones containing insert sequences which were expressed either constitutively or under developmental regulation. To achieve this, "early" and "late" stage RNA probes were prepared, labeled in a polynucleotide kinase reaction, and hybridized with the filter-bound DNAs.

a. Preparation of probes.

Total RNA was prepared from 1-inch green "early" and 3-inch intermediate "late" *L. esculentum* cv. UC82 fruit and subjected to oligo-dT cellulose chromatography for the selection of poly(A)+RNA essentially as described by Aviv and Leder [(1972) *Proc. Natl. Acad. Sci. USA* 69:1408–1412], but using LiCl for the binding instead of NaCl.

Poly(A)+ RNA prepared from early and late stages of *L. esculentum* cv. UC82 tomato fruit development was fractionated on a linear 5–20% sucrose gradient, and samples of RNA from gradient fractions were translated in an mRNA-dependent rabbit reticulocyte translation system by the method of Pelham and Jackson [(1976) *Eur. J. Biochem.* 67:247–256] to produce peptides labeled with L-($^{35}$S)-methionine [New England Nuclear (Boston, Mass.); October 1979 Manual]. Protein synthesis was assayed by determining the incorporation of TCA-precipitable label [Pelham and Jackson (1976) *Eur. J. Biochem.* 67:247–256], and the translation products were analyzed by electrophoresis on a 12.5% SDS acrylamide gel [Laemmli (1970) *Nature* 227:680–685] and fluorography.

b. Library screening.

Replica filters were prepared and the plasmids amplified [Hanahan and Meselson (1980) *Gene* 10:63–67] using 200 μg/ml chloramphenicol. DNA from cDNA clones was denatured, neutralized, and fixed to 150 mm nitrocellulose filters [Maniatis et al. (1982) *Molecular Cloning: A Laboratory Manual*, Cold Spring Harbor Laboratory Press, Cold Spring Harbor, N.Y.].

RNAs from a gradient fraction of one-inch green (early) RNA encoding proteins with a molecular mass of ~30–~60 kDa and from a similar gradient fraction of three-inch intermediate (late) RNA were labeled with $^{32}$P in a polynucleotide kinase (Boehringer-Mannheim, Milwaukee, Wis.) reaction. These labeled fruit RNAs were then hybridized to approximately 10,000 cDNA clones (a fraction of the complete cDNA library) bound to nitrocellulose filters. Of 313 clones which yielded strong hybridization signals, 36% contained insert sequences which appeared to be expressed differentially at the two different stages of development.

3. Identification of clone ptomUC82-3 as encoding a developmentally regulated protein.

Plasmid DNA was prepared from clones which yielded strong hybridization signals, labeled with $^{32}$P by nick translation and was used to probe northern blots of "early" and "late" fruit RNAs.

Total RNA was prepared from 1" green and 3" intermediate developmental stages of UC82 fruit as described above. RNA blots were prepared essentially as described by Thomas [(1980) *Proc. Natl. Acad. Sci. USA* 77:5201–5205], and separate panels of RNA were hybridized with $^{32}$P-labeled insert DNA from six cDNA clones. The autoradiographic patterns of hybridization indicated that clone ptomUC82-3 encodes a developmentally regulated, fruit-specific sequence which hybridized to a single RNA band with an apparent mobility of ~1.7 kb on a 1.5% agarose gel. These northern hybridization data, as well as hybridization/selection analyses, indicated that cDNA clone ptomUC82-3 corresponds to a gene which is expressed at low levels at early stages of fruit ripening, high levels at intermediate fruit ripening stages, and decreased levels in fully ripened fruit. The insert in ptomUC82-3, which was restriction-enzyme mapped and sequenced by the dideoxynucleotide chain termination method, was less than full-length cDNA clone but did contain an ATG start codon.

B. Isolation of the tomato HDC promoter.

A genomic library was constructed in λ FIX™II (Stratagene, La Jolla, Calif.) using DNA isolated from seedling tissue of *L. esculentum* cv. UC82, as described in Example 4A. The genomic library was screened with a 32P-labeled probe prepared from the 0.8 kb insert purified from cDNA ptomUC82-3 following digestion with PstI. The screening conditions were identical to those described in Example 2B and clones which hybridized to the probe were identified and plaque-purified.

One of the clones isolated from the genomic DNA library, λUC82-3.3, containing nucleic acids 1-4032 of Seq. ID No. 3, was shown by restriction enzyme mapping to contain putative regulatory regions upstream of the translation start site. A 3.7 kb SstI-BglII fragment from the 5' end of this clone was subcloned. Sequence analysis of the insert of this subclone revealed that it contains six exons that have 95–100% identity with comparable positions of cDNA ptomUC82-3 and appears to include a promoter region. A fragment containing the remaining 347 nt upstream from the SstI restriction site near the 5' end of the λUC82-3.3 insert was subcloned and sequenced.

The results of a sequence similarity search through the GenBank database release 67.0 and EMBL database release 26.0 [Devereaux et al. (1984) *Nucl. Acids Res.* 12:387–395] indicate a 60% similarity between the amino acid sequences predicted from cDNA clone ptomUC82-3 and the *Morganella morganii* bacterial histidine decarboxylase gene.

The promoter-containing region of λUC82-3.3, nucleotides 1–888 of Seq. ID No. 3, is herein referred to as the HDC promoter.

C. HDC promoter/tomato fruit invertase constructs

1. HDC/3-L1.1.

Construct HDC/3-L1.1 contains 538 bp of the HDC promoter region from AUC82-3.3 (nucleotides 349 to 886 of Seq. ID No. 3) fused to the *L. esculentum* cv. UC82 invertase cDNA pTOM3-L1 insert (nucleotides 1 to 2199 of Seq. ID No. 1), which is fused at the 3' end to the NOS (nopaline synthase) terminator.

pTOM3-L1 was digested with XhoI, made blunt-ended with T4 DNA polymerase, then digested with NotI to yield a 2202 bp fragment containing 3 nucleotides from the vector polylinker (AGC) plus the complete *L. esculentum* cv. UC82 invertase cDNA coding sequence (nucleotides 1 to 2199 of Seq. ID No. 1).

The above fragment from pTOM3-L1, the fragment containing the HDC promoter (nucleotides 349 to 886 of Seq. ID No. 3) were purified and ligated with NotI-, SstI-digested pGEM-11Zf(–) (Promega Corporation, Madison, Wis.). The resulting plasmid was called –540/3-L1.

The NOS terminator is contained in plasmid pBI101 (Clontech, Palo Alto, Calif.). Plasmid pBI101 was digested with SstI and Hind III and made blunt-ended with T4 DNA polymerase yielding an ¯10 kb vector fragment. The purified vector fragment was ligated to the DNA insert of –540/3-L1, which had been prepared by digestion with NotI and SstI and made blunt-ended with T4 DNA polymerase, to produce construct HDC/3L-1.1.

2. HDC/3-L1.2.

Construct HDC/3-L1.2 is identical to HDC/3-L1.1 except that it contains 886 bp of the HDC promoter region from λUC82-3.3 rather than 538 bp. Construct HDC/3-L1.2, thus, contains 886 bp of the HDC promoter region from λUC82-3.3 (nucleotides 1 to 886 of Seq. ID No. 3) fused to the tomato invertase gene (nucleotides 1 to 2199 of Seq. ID No. 1), which is fused at the 3' end to the NOS (nopaline synthase).

3. HDC/3-L1.3.

Construct HDC/3-L1.3 is identical to HDC/3-L1.1 except that it contains 690 bp of the HDC promoter region from λUC82-3.3 rather than 538 bp. Construct HDC/3-L1.3, thus, contains 690 bp of the HDC promoter region from λUC82-3.3 (nucleotides 1 to 690 of Seq. ID No. 3) fused to the *L. esculentum* cv. UC82 invertase cDNA (nucleotides 1 to 2199 of Seq. ID No. 1) which is fused at the 3' end to the NOS (nopaline synthase) terminator.

D. HDC-promoter/GUS constructs.

1. HDC/GUS.1.

Construct HDC/GUS.1 contains a promoter fragment from λUC82-3.3 which extends from 794 to 3 bp upstream of the ATG start codon (nucleotides 94 to 886 in Seq. ID No. 3) fused to the *E. coli* GUS gene.

Plasmid pUC82-3.3NH was digested with DdeI, the ends of the resultant fragment were filled in with Klenow DNA polymerase, and the 792 bp fragment was isolated and purified. Plasmid pUC82-3.3NH was constructed by inserting the 3.4 kb restriction enzyme fragment, which extends from the NotI site in the vector polylinker to the first HindIII site from the 5' end of the λUC82-3.3 insert, into the NotI and HindIII sites of pGEM-11Zf(–) (Promega Corporation, Madison, Wis.) to produce pUC82-3.3 NH.

Plasmid pBI101.3/pUC was made by inserting the 2200 bp EcoRI-HindIII fragment of pBI101.3 (Clontech, Palo Alto, Calif.) into EcoRI-HindIII-digested pUC119 [Vieira and Messing (1987) In *Methods in Enzymology*, R. Wu and L. Grossman, Eds., Vol. 153, pp. 3–11, Academic Press, New York]. The 792 bp fragment was ligated to pBI101.3/pUC which had been digested with HindIII and BamHI, and the resulting plasmid was called –790/GUS.

The 3 kb EcoRI-HindIII fragment containing the HDC promoter-GUS fusion was isolated from –790/GUS and ligated to EcoRI- and HindIII-digested pBIN19 to produce HDC/GUS.1.

2. HDC/GUS 2

Construct HDC/GUS.2 contains 690 bp of the HDC promoter region from λUC82-3.3 (nucleotides 1 to 690 of Seq. ID No. 3) fused to the *E. coli* GUS gene.

Plasmid pUC82-3.3NH was digested with XbaI and SspI, and the 710 bp fragment was isolated and purified. The 710 bp fragment was ligated to purified XbaI- and SmaI-digested pBI101.3/pUC to create –690/GUS. The 2.9 kb EcoRI-HindIII fragment containing the HDC promoter-GUS fusion was isolated from –690/GUS and ligated to EcoRI- and HindIII-digested pBIN19 to produce HDC/GUS.2.

EXAMPLE 9

TRANSFORMATION OF *L. ESCULENTUM* WITH HDC PROMOTER CONSTRUCTS AND ANALYSIS FOR RECOMBINANT GENE EXPRESSION.

The transformation of seedlings grown from *L. esculentum* cv. UC82 seeds was performed essentially by the protocol of Fillatti et al. [(1987) *Bio/Technology* 5:726–730], as described in Example 7.

Invertase and GUS expression in the fruit of transformed tomato plants may be assayed as described in Example 7.

EXAMPLE 10

INVERTASE C-TERMINAL/GUS CONSTRUCTS

Two constructs have been assembled using the singal and targeting sequences from secreted proteins. The first of these constructs (35S/GUS44) was assembled to express a fusion protein with the signal sequence from phytohemagglutinin-L (PHA) fused to the amino-terminus of *E. coli* GUS and was designed to allow GUS to be targeted to the endoplasmic reticulum and then secreted. The second construct (35S/GUS-INV) incorporates the C-terminus of tomato fruit vacuolar invertase into GUS and should target GUS to the vacuole.

35S/GUS44 was constructed from plasmid pA35/PHIN44 [Dickinson et al. (1991) *Plant Physiol.* 95:420–525]. The yeast invertase coding sequence in pA35/PHIN44 was replaced by the GUS coding sequence of plasmid pGUSN358→S (Clontech, Palo Alto, Calif.) by digesting pA35/PHIN44 with SphI and ligating this vector with a SphI-digested fragment derived from PCR amplification of plasmid pGUSN358→S, using Seq. ID No. 7, which anneals to the 5' end of the GUS gene coding sequence, and Seq. ID No. 8, which anneals to the 3' end of the GUS gene coding sequence, as primers.

The 1.8 kb fragment obtained after PCR amplification of pGUSN358→S was digested with SphI and ligated into pA35/pHIN44 to produce plasmid 35S/GUS44. This plasmid contains the following noteworthy features: 1) a cauliflower mosaic virus promoter, CaMV 35S, for high-level expression; 2) the coding sequence for the first 44 amino acids of PHA-L which includes the 20 amino acid signal sequence for efficient translocation across the ER membrane; 3) the GUS reporter protein coding sequence fused in-frame with the PHA sequence and modified by deletion of a glycosylation site that allows GUS to move through secretory system; 4) a unique PstI restriction site which immediately precedes the termination codon of GUS for in-frame C-terminal fusions; and 5) an octopine synthase transcriptional terminator. Upon introduction of this construct into a plant, active GUS which is secreted by the default pathway to the plant cell wall should be produced.

To demonstrate the ability of the C-terminus of tomato invertase to target heterologous proteins to the vacuole, the coding sequences for the last 39 amino acids of tomato invertase (amino acids 598–636 in Seq. ID No. 1) were fused in-frame to the 3' end of the GUS gene contained in plasmid 35S/GUS44.

First, plasmid 35S/3L-1b was constructed to place the OCS transcriptional terminator after the invertase cDNA sequence and to thereby facilitate subsequent steps. Plasmid pTOM3-L1 was digested with NotI, filled in with Klenow DNA polymerase, digested with XhoI, and the 2.2 kb fragment was purified and cloned into the CaMV 35S promoter/OCS terminator vector pA35. Plasmid pA35 was prepared for this cloning by digesting with SphI, filling-in with Klenow DNA polymerase, and then digesting with SalI. The resulting clone was named 35S/3L-1b and was used for PCR amplification of the 3' end of the invertase sequence.

For amplification of a fragment containing the 3' end of the 35S/3L-1b insert, a synthetic oligonucleotide was designed which included a new PstI restriction site to facilitate the in-frame fusion of GUS and invertase sequences. The sequence of one primer was Seq. ID No. 9. The second primer was the pUC/M13 reverse primer (New England Biolabs, Inc., Beverly, Mass.). Amplification by PCR was conducted according to the procedure of Perkin-Elmer/Cetus (Norwalk, Conn.). The resultant 600 bp fragment was then digested with PstI and HindIII and ligated into 35S/GUS44, which had been digested with PstI and HindIII and purified, to produce plasmid 35S/GUS-INV.

These constructs are transformed into tomato tissue by methods described in Example 7. The resulting transformed plants are then assayed for GUS activity as described in Example 7.

EXAMPLE 11

CaMV 35S PROMOTER/TOMATO FRUIT INVERTASE CONSTRUCTS

35S/3-L1/BIN Overproducing construct.

1. Construction.

The cDNA sequence encoding tomato fruit vacuolar invertase (nucleotides 1–2199 of Seq. ID No. 1) was inserted between the CaMV 35S promoter and the nopaline synthase (NOS) terminator in vector pCAMVCN (Pharmacia LKB Biotechnology, Piscataway, N.J.). Plasmid pCAMVCN was digested with PstI, blunt-ended with T4 DNA polymerase, purified, and ligated with the purified 2202 bp XhoI-NotI fragment of pTOM3-LI, which was also made blunt-ended with T4 polymerase. The resulting clone, named 35S/3-L1, was ligated into pBIN19 as a cassette fragment containing the CaMV 35S promoter, the invertase cDNA sequence, and the NOS terminator, to produce 35S/3-L1/BIN. This subcloning was performed by digesting 35S/3-L1 at the 3' end with BglII and at the 5' end with a partial XbaI digestion. The 3.0 kb fragment was purified and ligated into pBIN19 prepared by digestion with XbaI and BamHI.

2. Transformation and expression.

Seedlings grown from seeds of *L. esculentum* cv. UC82 were transformed with 35S/3-L1/BIN essentially by the protocol of Fillatti et al. [(1987) *Bio/Technology* 5:726–730], as described in Example 7. To determine the level of invertase activity in plants generated from the transformed seedlings, mature leaf tissue from the transgenic plants and control non-transgenic plants that had been growing in soil for two months was assayed as follows. Tissue samples (1 g) were homogenized in a mortar and pestle with 2 ml homogenization buffer (0.25M Tris phosphate, pH 7.6, containing 1 mM EDTA and 5 mM DTT). All steps were performed at 4° C. Homogenates were centrifuged for 10 min at 14,000× g and the supernatant was stored on ice. Leaf extracts were adjusted to contain equal concentrations of protein, which were determined by the Bradford Reagent method (BioRad Laboratories, Richmond, Calif.). Samples of the leaf extracts were analyzed in invertase activity gels, which were performed according to the method of Gabriel and Wang [(1969) *Anal. Biochem.* 27:545–554], as modified by Carlson et al. [(1981) *Genetics* 98:25–40]. Purified tomato fruit invertase was used as a positive control in these assays.

Tomato plants transformed with 35S/3-L1/BIN were shown to contain high levels of invertase activity in their leaves. With the conditions used for the extraction and assay, no invertase activity was detected in extracts from non-transgenic tomato leaves.

B. Antisense construct 35/3-L1(−).

An antisense invertase construct designed to reduce expression of vacuolar invertase in tomato fruit has been prepared. The vacuolar tomato fruit invertase clone pTOM3-L1 cDNA insert (nucleotides 1–2199 of Seq. ID No. 1) was inserted into the CaMV 35S promoter/terminator cassette in the reverse orientation to create 35S/3-L1(−). pTOM-3-L1 was digested with NotI, blunt-ended, digested with XhoI, and the 2202 bp fragment was purified and cloned into pA35 prepared by digestion with SmaI and SalI. 35S/3-L1(−) contains the CaMV 35S promoter fused to an antisense pTOM3-L1 cDNA and the OCS transcriptional terminator. This fusion construct was ligated as an EcoRI-SstI fragment into the corresponding sites of pBIN19 to yield plasmid 35S/3-L1(−)BIN.

c. Cosuppression construct 35B/3-L1(P).

A construct for use in cosuppression of endogenous invertase expression was constructed by removing a coding segment from 35S/3-L1 to create a construct 35S/3-L1(P) which encodes a truncated, nonfunctional protein. To prepare construct 35S/3-L1(P), 35S/3-L1 was digested with PstI, which digests at two sites (nucleotides 1205 and 1386 in Seq. ID No. 1) within the invertase coding region, and religated. This produced a 181 bp deletion, creating a shift in the reading frame after codon 400 in Seq. ID No. 1 and the introduction of a stop codon four codons downstream.

Using the same strategy as described above for 35S/3-L1/BIN, 35S/3-L1(P) was mobilized into pBIN19 as an XbaI fragment (obtained following a partial digestion) to create 35S/3-L1(P)BIN.

Transgenic plants that contain this construct should express reduced levels of invertase compared to a non-transgenic plant of the same species.

Since modifications will be apparent to those of skill in the art, it is intended that this invention be limited only by the scope of the appended claims.

---

That which is claimed is:

1. An isolated DNA sequence which comprises a tomato vacuolar invertase promoter region having the nucleotide sequence set forth in nucleotides 1-3519 of Sequence ID No. 2 or a fragment thereof which is capable of controlling the transcription of a coding sequence which is operatively linked thereto.

2. The DNA sequence of claim 1, which comprises nucleotides 2773-3519 of Sequence ID No. 2 or a fragment thereof which is capable of controlling the transcription of a coding sequence which is operatively linked thereto.

3. The DNA sequence of claim 1, which comprises nucleotides 2441-3519 Sequence ID No. 2 or a fragment thereof which is capable of controlling the transcription of a coding sequence which is operatively linked thereto.

4. An isolated DNA sequence which comprises nucleotides 1-3679 of Sequence ID No. 4 or a fragment thereof which is capable of controlling the transcription of a coding sequence which is operatively linked thereto.

5. The isolated DNA sequence of claim 1, which is operatively linked in proper reading frame to a desired coding sequence.

6. The isolated DNA sequence of claim 2, which is operatively linked in proper reading frame to a desired coding sequence.

7. The isolated DNA sequence of claim 3, which is operatively linked in proper reading frame to a desired coding sequence.

8. The isolated DNA sequence of claim 4, which is operatively linked in proper reading frame to a desired coding sequence.

9. A method for producing a desired protein or polypeptide by expression of a DNA sequence encoding said protein or polypeptide comprising expressing said DNA coding sequence in a recombinant host cell under the transcriptional control of an isolated DNA sequence according to claim 1.

10. A method for producing a desired protein or polypeptide by expression of a DNA sequence encoding said protein or polypeptide comprising expressing a DNA coding sequence in a recombinant host cell under the transcriptional control of an isolated DNA sequence according to claim 2.

11. A method for producing a desired protein or polypeptide by expression of a DNA sequence encoding said protein or polypeptide comprising expressing said DNA coding sequence in a recombinant host cell under the transcriptional control of an isolated DNA sequence according to claim 3.

12. A method for producing a desired protein or polypeptide by expression of a DNA sequence encoding said protein or polypeptide comprising expressing said DNA coding sequence in a recombinant host cell under the transcriptional control of an isolated EDNA sequence according to claim 4.

13. A method for producing a desired protein or polypeptide by expression of a DNA sequence encoding said protein or polypeptide comprising expressing said DNA coding sequence under the transcriptional control of a promoter sequence contained in nucleotides 1-3519 of Sequence ID No. 2 or a promoter sequence contained in nucleotides 1-3679 of Sequence ID No. 4 wherein said DNA coding sequence is not normally associated with this promoter sequence.

* * * * *